US008465542B2

(12) United States Patent
Levy et al.

(10) Patent No.: US 8,465,542 B2
(45) Date of Patent: *Jun. 18, 2013

(54) STEROID LIPID-MODIFIED POLYURETHANE AS AN IMPLANTABLE BIOMATERIAL, THE PREPARATION AND USES THEREOF

(75) Inventors: Robert J. Levy, Merion Station, PA (US); Ivan Alferiev, Clementon, NJ (US); Stanley J. Stachelek, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/487,984

(22) Filed: Jun. 4, 2012

(65) Prior Publication Data
US 2012/0316295 A1 Dec. 13, 2012

Related U.S. Application Data

(63) Continuation of application No. 12/143,275, filed on Jun. 20, 2008, now Pat. No. 8,193,290, which is a continuation of application No. 10/521,994, filed as application No. PCT/US2004/021831 on Jul. 8, 2004, now Pat. No. 7,408,014.

(60) Provisional application No. 60/485,486, filed on Jul. 8, 2003.

(51) Int. Cl.
*A61F 2/24* (2006.01)
*A61F 2/06* (2006.01)

(52) U.S. Cl.
USPC ............. 623/2.42; 623/1.41; 528/65; 528/75; 528/373; 527/204; 527/200

(58) Field of Classification Search
USPC ..... 623/1.41, 2.42; 528/65, 75, 373; 527/204, 527/200
See application file for complete search history.

(56) References Cited

U.S. PATENT DOCUMENTS

| 3,515,734 A | 6/1970 | Craig |
| 4,316,041 A | 2/1982 | Totten et al. |
| 4,521,564 A | 6/1985 | Solomon et al. |
| 4,539,716 A | 9/1985 | Bell |
| 4,546,500 A | 10/1985 | Bell |
| 4,642,242 A | 2/1987 | Solomon et al. |
| 4,745,136 A | 5/1988 | Thomas et al. |
| 4,746,654 A | 5/1988 | Breliere et al. |
| 4,804,382 A | 2/1989 | Turina et al. |
| 4,883,755 A | 11/1989 | Carabasi et al. |

(Continued)

FOREIGN PATENT DOCUMENTS
WO  WO 95/20008  7/1995

OTHER PUBLICATIONS

J. Hoch, et al. "In Vitro Endothelialization of an Aldehyde-Stabilized Native Vessel," J. Surg. Res. 44:545-554 (1998).

(Continued)

*Primary Examiner* — Michael L Leonard
(74) *Attorney, Agent, or Firm* — RatnerPrestia

(57) ABSTRACT

A modified polyurethane including a lipid substituent pendant from at least one urethane nitrogen and/or at least one carbon atom of the modified polyurethane, methods of preparing modified polyurethanes and the use thereof as an implantable biomaterial.

4 Claims, 20 Drawing Sheets
(2 of 20 Drawing Sheet(s) Filed in Color)

U.S. PATENT DOCUMENTS

| | | | |
|---|---|---|---|
| 4,960,423 | A | 10/1990 | Smith |
| 5,037,378 | A | 8/1991 | Muller et al. |
| 5,073,575 | A | 12/1991 | Blanch et al. |
| 5,131,907 | A | 7/1992 | Williams et al. |
| 5,134,035 | A | 7/1992 | Kumar |
| 5,159,050 | A | 10/1992 | Onwumere |
| 5,403,750 | A | 4/1995 | Braatz et al. |
| 5,624,975 | A | 4/1997 | Valencia |
| 5,674,722 | A | 10/1997 | Mulligan et al. |
| 5,723,324 | A | 3/1998 | Bowlin |
| 5,766,584 | A | 6/1998 | Edelman et al. |
| 5,785,965 | A | 7/1998 | Pratt et al. |
| 5,855,618 | A | 1/1999 | Patnaik |
| 5,879,383 | A | 3/1999 | Bruchman et al. |
| 6,320,011 | B1 | 11/2001 | Levy et al. |
| 6,689,681 | B2 | 2/2004 | Watanabe |
| 6,733,747 | B2 | 5/2004 | Anderson |
| 6,890,998 | B2 | 5/2005 | Alferiev et al. |
| 6,900,282 | B2 | 5/2005 | Alferiev et al. |
| 2002/0045263 | A1 | 4/2002 | Leong et al. |
| 2006/0063894 | A1 | 3/2006 | Alferiev et al. |

OTHER PUBLICATIONS

J. Hoch, et al. "Endothelial Cell Interactions with Native Surfaces," Ann. Vasc. Surg. 2:153-159 (1989).

P.A. Schneider, et al. "Confluent durable endothelializaiton of endarterectomized baboon aorta by early attachment of cultured endothelial cells," J. Vasc. Surg. 11:365-372 (1990).

Dardik, et al. "Chronic in vitro shear stress stimulates endothelial cell retention on prosthetic vascular grafts and reduces subsequent in vivo neointimal thickness," J. Vasc. Surg. 29:157-167 (1999).

Ballerman, et al. "Adhesion and Differentiation of endothelial Cells by Exposure to Chronic Shear Stress: A Vascualr Graft Model," Blood Purif 13:125-134 (1995).

Ott, et al. "Shear stress-conditioned, endothelial cell-seeded vascular grafts: Improved cell adherence in response to in vitro shear stress" Surgery 117:334-339.

Kan, et al. "Rates of Spontaneous Exchange of Synthetic Radiolabeled Sterols between Lipid Vesicles" Biochemistry 31(6) 1866-1874 (1992).

Gimbrone, M., "Culture of Vascular Endothelium" Progress Hemostasis and Thrombosis 3:1-28 (1976).

Lalka, et al. "Acellular Vascular Matrix: A Natural Endothelial Cell Substrate" Ann. Vasc. Surg. 2:108-117 (1989).

I. S. Alferiev, et al., "Novel Elastomeric Polyurethanes with Pendant Epoxy Groups as Highly Reactive Auxiliary Groups for Further Derivatizations", J. Polym. Sci., Part A: Polym. Chem., 40:4378-4385 (2002).

I. Alferiev, et al., "Elastomeric Polyurethanes Modified With Geminal Bis-Phosphonate Groups," J. Polym. Sci., Part A: Polym. Chem., 39:105-116 (2001).

Nakaya, T., et al. "Synthesis and characterization of polyurethane containing cholesterol and phosphatidylcholine analogous moieties," Macromol. Rapid Commun. 16, 253-258 (1995).

Cholesterol-modified Tecothane

R = polyether-urethane macromolecule

BAEC attachment to substrate (25 dynes/cm$^2$)

R = polyurethane macromolecule, Su = N-succinimidyl, DCC = dicyclohexylcarbodiimide, A = p-C$_6$H$_4$CH$_2$C$_6$H$_4$-p (polyurethanes based on MDI) or
cyclo-C$_6$H$_{10}$CH$_2$C$_6$H$_{10}$-cyclo (aliphatic polyurethanes based on HMDI)
X = residue of polytetramethyleneoxide (polyether-urethanes) or
polycarbonatediol (polycarbonate-urethanes)

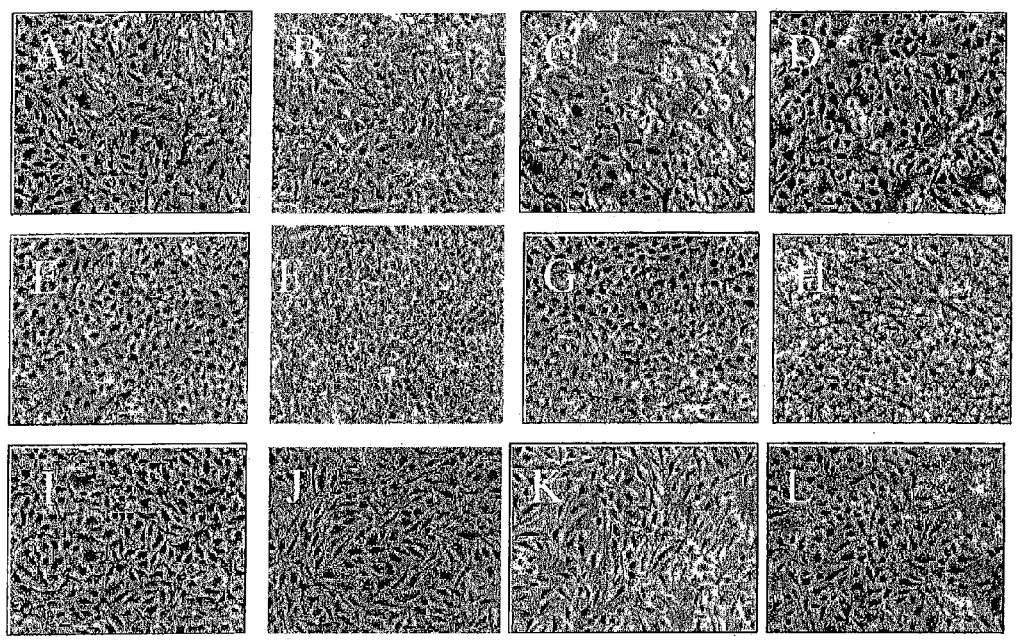
Figures 13A-L

Figures 14A-L
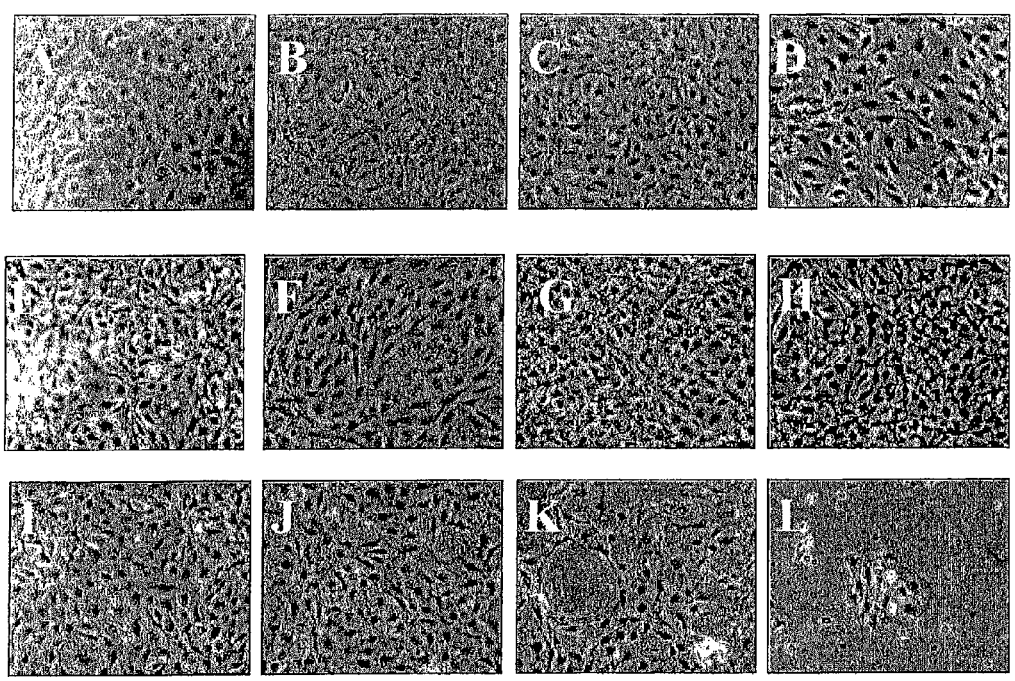

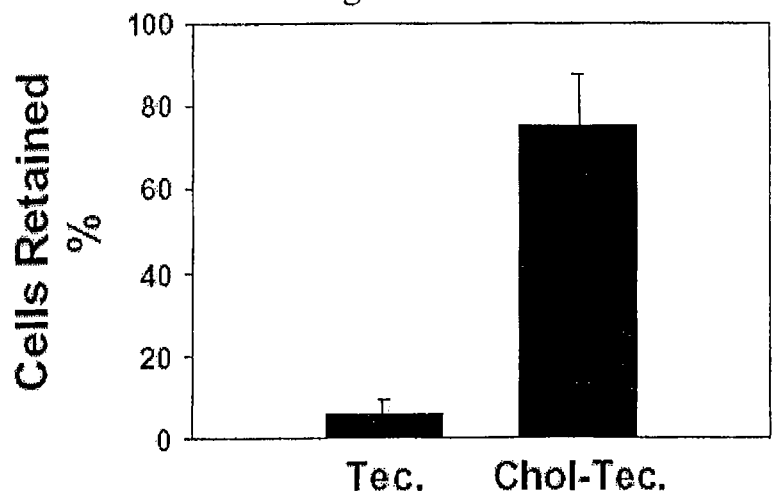
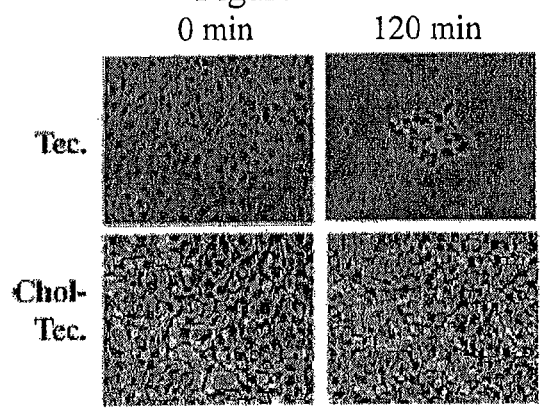

STEROID LIPID-MODIFIED POLYURETHANE AS AN IMPLANTABLE BIOMATERIAL, THE PREPARATION AND USES THEREOF

CROSS-REFERENCE TO RELATED APPLICATIONS

This application is a continuation of U.S. application Ser. No. 12/143,275, filed Jun. 20, 2008 which is a continuation of U.S. application Ser. No. 10/521,994, filed Jan. 19, 2005, now U.S. Pat. No. 7,408,014, which is a national stage entry of International Application No. PCT/US2004/021831, filed Jul. 8, 2004, which claims the benefit of priority of U.S. application Ser. No. 60/485,486, filed Jul. 8, 2003. This application claims the benefit of priority of all the foregoing applications and incorporates their content by reference herein in their entirety.

STATEMENT REGARDING FEDERALLY SPONSORED RESEARCH OR DEVELOPMENT

This research was supported in part by U.S. Government funds (National Heart, Lung and Blood Institute grant number HL 59730), and the U.S. Government may therefore have certain rights in the invention.

BACKGROUND OF THE INVENTION

1. Field of Invention

This invention relates to polyurethanes modified to retain epithelial cells. Particularly, it relates to implants made from such polyurethane . . . .

2. Description of Related Art

Polyurethanes, i.e. polymers which comprise repeating units having a urethane group in the polymer backbone, can be used to form bulk polymers, coatings, fillings, and films. Notably, polyurethanes are also readily machinable once set. These properties of polyurethanes have rendered them useful for medical and non-medical purposes.

With regard to medical applications, polyurethanes are widely used in implants, particularly cardiovascular implants, as highly biocompatible biomaterials. For example, polyurethanes have been employed in the manufacture of pacemaker electrodes, vascular grafts, and artificial heart valves.

Medical uses of polyurethanes have, however, been heretofore limited by, among other reasons, the tendency of polyurethane products which contact the blood stream or other biological fluids to calcify, induce thrombogenesis, and/or impede cellular attachment and growth. Promotion of cell adhesion on medical devices comprising polyurethane is of particular concern, as the establishment of a confluent monolayer of endothelial cells is critical for neovascularization (Simionescu, N. and N. Simionescu, eds. Endothelial Cell Dysfunctions. 1992. New York:Plenum Press). Additionally, the cellular attachment to vascular grafts or implants must be strong enough to withstand the fluid shear stress exerted by blood and other biological fluids. Modified polyurethane surfaces currently available, such as those that have been deliberately textured or cast as foams, have provided for only disorganized cell growth. Polyurethane surfaces have also been coated with fibronectin and collagen which are potent ligands for cell surface receptors. Despite promoting cell adhesion, fibronectin and collagen coated polyurethanes are not ideal modifications because apoptosis and calcification of vascular cells has been observed when cultivated on collagen coated matrices and vascular cells seeded on fibronectin coated polyurethane failed to thrive.

As those skilled in the art will appreciate, a need exists for implantable devices comprising polyurethane which allows for enhanced cellular attachment and growth.

Natural blood contact surfaces, such as those found within blood vessels, possess mechanisms that prevent blood from clotting during normal passage along the surface. In the case of a mammalian artery, the immediate blood contact surface comprises a layer of non-thrombogenic ECs. Immediately external to the EC layer is the remainder of the intima: a subendothelial matrix layer of basement membrane and underlying glycoprotein-bearing extracellular matrix, and the internal elastic lamina. Surrounding the intima layer is the multilaminate media structure containing smooth muscle cells (SMCs) and elastin, and surrounding this media is the adventitia, the most external layer comprised of fibroblasts and connective tissue. Both the subendothelial layer and media are generally considered to be thrombogenic in nature in order to maintain hemostasis when the vascular system is injured.

Intact endothelial linings are considered to be non-thrombogenic unless damaged. Because of their blood-contacting location, ECs have been thoroughly investigated with respect to their anti-thrombogenic function. ECs are known to synthesize or bind a number of substances with coagulation-inhibiting or fibrinolytic function including heparan sulfate/antithrombin III, dermatan sulfate/heparin cofactor II, thrombomodulin/protein C/protein S, prostacyclin and tissue-type plasminogen activator. Furthermore, segments of endothelium-bearing autologous vessel transplanted from one site to another in an individual to bypass diseased vessels exhibit an incidence of thrombosis substantially less than that of synthetics used in the same application. For these reasons, it has been assumed that ECs are responsible for the non-thrombogenic activity of vessels. According to this assumption, synthetic blood contact devices capable of thrombo-resistance similar to the native vasculature would require a blood contact surface of ECs.

Numerous attempts have been made to provide prosthetic surfaces, and specifically vascular grafts, that include or develop an EC lining as described in U.S. Pat. No. 5,879,383 to Bruchman et al. The overwhelming majority of these attempts have been carried out as an intraoperative cell-seeding procedure. Intraoperative cell-seeding typically involves harvesting ECs from the recipient during the procedure and immediately seeding these collected cells onto a vascular graft that has been pretreated with a substrate to enhance EC attachment. Substrates frequently applied to the synthetic surface include preclotted blood taken from the patient or extracellular matrix proteins such as fibronecfin, collagen, or laminin, either singly or in combination. This approach was first reported by M. B. Herring et al. in "A single staged technique for seeding vascular grafts with autogenous endothelium," Surgery 84:498-504 (1978). In this procedure, autologous cells were seeded onto a preclotted DACRON™ graft. These seeded grafts demonstrated a decreased thrombus formation compared to control grafts without ECs. In spite of the improved initial adherence of the cells to the synthetic surface afforded through the use of these various substrata, the shear forces resulting from blood flow nevertheless leads to the loss of a substantial fraction of the applied cells.

In a variation of the above, U.S. Pat. No. 4,960,423 to Smith describes the use of elastin-derived peptides to enhance EC attachment. Some studies have used combinations of extracellular matrix molecules and cells to provide a substrate for EC attachment and growth. For example, U.S. Pat. Nos. 4,539,716 and 4,546,500 to Bell describe means by which ECs are grown on a living smooth muscle cell-collagen lattice. In addition, U.S. Pat. No. 4,883,755 to Carabasi et al. describes a technical method for seeding ECs onto damaged blood vessel surfaces.

Alternative means of growing ECs on vascular grafts have also been reported. For example, the use of physical force to apply ECs to graft surfaces is described in U.S. Pat. No. 5,037,378 to Muller et al. In another example, U.S. Pat. No. 4,804,382 to Turina and Bittman describe the application of ECs to a semi-permeable membrane in which the pores are filled with aqueous gels to allow EC coverage.

Another approach has been the seeding of ECs onto biologically-derived surfaces, including pericardium, cardiac valve leaflets, amnion, and arteries. These efforts appear to have originated with J. Hoch et al. in "In vitro endothelialization of an aldehyde-stabilized native vessel," J. Surg. Res. 44:545-554 (1988), where the authors attempted to grow endothelium on ficin-digested, dialdehyde stabilized, bovine artery. Human venous ECs were found to adhere to and spread on the remnant collagen surface of these enzyme-digested grafts, but no implant studies were performed. J. Hoch et al. also investigated the growth of endothelium on human amnion, on live, mechanically-scraped human artery, and again on ficin-digested, tanned bovine artery. (J. Hoch et al., "Endothelial cell interactions with native surfaces," Ann. Vasc. Surg. 2:153-159 (1989)). Although EC adhesion was observed on these surfaces by 2 hours, the longterm persistence of ECs on these surfaces was not examined, and, as in the previous study, none of these endothelialized materials were implanted as vascular substitutes. Schneider et al. showed that ECs could be successfully seeded onto the remaining collagenous surface of baboon vessels from which the intima was removed. (P. A. Schneider et al., "Confluent durable endothelialization of endarterectomized baboon aorta by early attachment of cultured endothelial cells," J. Vasc. Surg. 11:365-372 (1990)). Lalka et al, used detergent extraction of canine arteries to produce an ethanol-fixed acellular vascular matrix onto which human umbilical vein ECs were successfully seeded in vitro. (S. G. Lalka et al., "Acellular vascular matrix: A natural endothelial cell substrate," Ann. Vasc. Surg. 2:108-117 (1989)).

Although a small number of grafts seeded lumenally with ECs have been implanted clinically outside of the United States, and improved patencies over non-seeded grafts have been observed, this approach has generally enjoyed mixed success, and the concept still faces many challenges as described in U.S. Pat. No. 6,733,747 to Anderson et al. First, it is necessary that the cells used to seed the graft be autologous or otherwise non-immunogenic to avoid recognition and destruction of the cells by the patient's immune system. To obtain autologous ECs from a patient, the cells must be harvested from an isolated blood vessel. The harvesting surgical procedure not only increases prosthetic implant preparation time, but can also lead to complications and discomfort for the patient.

Second, retention of the cells on the graft surface after implantation has been an issue. A number of methods have been disclosed to address this issue, and include forcible injection of ECs into the graft, preclotting and seeding the lumenal surface of the graft, static adhesion-seeding of the lumen, vacuum seeding of the lumen, seeding the lumen in an extracellular matrix, and seeding of the lumen using electrostatic and gravitational forces. These methods are reviewed or disclosed in more detail in U.S. Pat. No. 5,723,324 to Bowlin et al. Additionally, it has been suggested that flow conditioning the seeded graft in vitro prior to implantation would improve cell retention by allowing the cells to secrete adhesion factors in response to slowly increasing shear rates (Dardik et al., 1999, J Vasc Surg 29: 157-67; Ballerman et al., 1995, Blood Purif 13: 125-34; and Ott and Ballerman, 1995, Surgery 117: 334-9). Although there is some evidence that methods such as conditioning may improve cell retention, all of these methods add yet another level of complexity to the seeding process and it is still not clear that significantly improved cellular retention can be achieved.

Thus, there remains a need in the art for a better EC seeding technique of prostheses in order to provide long-term patency and eventual healing by inhibiting thrombosis and inflammatory cell interactions. The instant invention provides a novel method of EC seeding by utilizing a cholesterol modified polyurethane surface to which the ECs can attach.

All references cited herein are incorporated herein by reference in their entireties.

BRIEF SUMMARY OF THE INVENTION

The invention is aimed at utilizing endothelial seeding of polyurethane heart valve cusps as a cell therapy approach for inhibiting thrombosis and inflammatory cell interactions. The inventors have discovered that cholesterol modification results in a polyurethane surface with membrane-lipid like properties that would facilitate cellular adhesion, thereby permitting robust endothelial cell seeding of polyurethane surfaces. The rationale for choosing cholesterol was based on several considerations including cholesterol's resistance to enzymatic degradation, and cholesterol's hydrophobicity, which could hypothetically facilitate strong associations between cholesterol modified polyurethane and cellular plasma membranes[6]. Accordingly, the invention provides modified polyurethane comprising a lipid substituent pendant from at least one urethane nitrogen and/or at least one carbon atom of the modified polyurethane.

In certain embodiments, the lipid substituent is a steroid lipid substituent. In certain embodiments, the steroid lipid substituent is a member selected from the group consisting of a thiol-modified cholesterol substituent, an amino-modified cholesterol substituent, a carboxy-modified cholesterol substituent, and an epoxy-modified cholesterol substituent. In certain embodiments, the thiol-modified cholesterol substituent is a 3-mercapto-2-hydroxypropyl-cholesterol.

In certain embodiments, the modified polyurethane further comprises a linker moiety between (1) the steroid lipid substituent and (2) the at least one urethane nitrogen and/or the at least one carbon atom of the modified polyurethane, wherein the linker moiety covalently binds the steroid lipid substituent with the at least one urethane nitrogen and/or the at least one carbon atom. In certain embodiments, the linker moiety is an (n+1)-valent organic radical comprising at least one carbon atom. In certain embodiments, the linker moiety is a bivalent organic radical selected from the group consisting of $C_1$ to $C_{18}$ alkylene, $C_1$ to $C_{18}$ alkyleneamino, $C_1$ to $C_{18}$ alkyleneoxy, $C_1$ to $C_{18}$ haloalkylene, $C_2$ to $C_{18}$ alkenylene, $C_6$ to $C_{18}$ arylene, a modified $C_2$ to $C_{18}$ alkenylene having at least one carbon substituted by a halogen group, $C_2$ to $C_{18}$ alkenylene having one or more O, S, or N atoms incorporated into an alkenylene chain, a bivalent heterocyclic radical, and mixtures thereof. Preferably, the linker moiety is $C_1$ to $C_6$ alkylene. More preferably, the linker moiety is butylene.

In certain embodiments, the lipid substituent is a thiol-modified cholesterol substituent bound to the at least one urethane nitrogen and wherein said modified polyurethane has a formula:

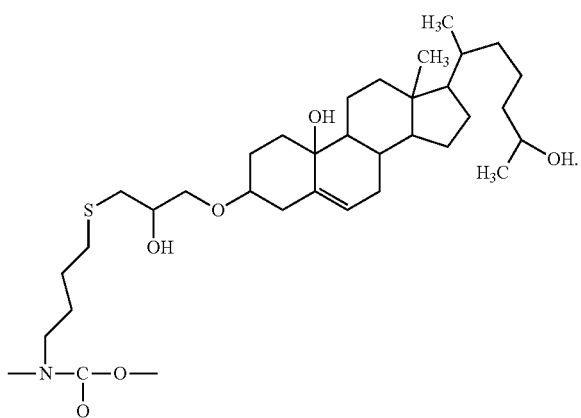 [SMILES: COC(O)N(C)CCCCSCC(O)COC1CCC2(O)C(=CCC3C2CCC2(C)C(C(C)CCCC(C)O)CCC32)C1]

In certain embodiments, the lipid substituent is pendant from about 0.5 to about 50% of urethane nitrogen atoms and/or about 0.5 to about 50% of carbon atoms.

In certain embodiments, the lipid substituent is pendant from 1 to 20% of urethane nitrogen atoms and/or 1 to 20% of carbon atoms. In certain embodiments, the lipid substituent is pendant from 5 to 10% of urethane nitrogen atoms and/or 5 to 10% of carbon atoms. In certain embodiments, the modified polyurethane comprises at least about 10 micromoles of the lipid substituent per gram of the modified polyurethane.

In certain embodiments, the modified polyurethane has at least two different lipid substituents pendant from urethane nitrogen atoms and/or carbon atoms.

Advantageously, said modified polyurethane is less prone to degradative oxidation than a polyurethane.

Also provided is a process for preparing the modified polyurethane of the invention, the process comprising: providing a polyurethane comprising a urethane amino moiety and at least one carbon; providing a multifunctional linker reagent of a formula:

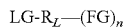

wherein n is an integer from 1 to 3, FG is a functional group selected from the group consisting of a halogen, a carboxyl group, a sulfonate ester, and an epoxy group, LG is a leaving group selected from the group consisting of a halogen, a carboxyl group, a sulfonate ester, and an epoxy group, and $R_L$ is an (n+1)-valent organic radical comprising at least one carbon atom; providing a lipid comprising the lipid substituent;

reacting the multifunctional linker reagent with the urethane amino moiety to form a polyurethane substituted with at least one substituent group of a formula

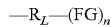

reacting the lipid and the polyurethane substituted with the at least one substituent group to form the modified polyurethane.

In certain embodiments, $R_L$ is a bivalent organic radical selected from the group consisting of $C_1$ to $C_{18}$ alkylene, $C_1$ to $C_{18}$ alkyleneamino, $C_1$ to $C_{18}$ alkyleneoxy, $C_1$ to $C_{18}$ haloalkylene, $C_2$ to $C_{18}$ alkenylene, $C_6$ to $C_{18}$ arylene, a modified $C_2$ to $C_{18}$ alkenylene having at least one carbon substituted by a halogen group, $C_2$ to $C_{18}$ alkenylene having one or more O, S, or N atoms incorporated into an alkenylene chain, a bivalent heterocyclic radical, and mixtures thereof.

In certain embodiments, the multifunctional linker reagent is a member selected from the group consisting of a dibromoalkyl compound, a bromo-carboxyalkyl compound, and a bromo-epoxyalkyl compound.

In certain embodiments, the lipid comprises a steroid lipid and the lipid substituent comprises a steroid lipid substituent.

In certain embodiments, the steroid lipid comprises modified cholesterol and the steroid lipid substituent is a member selected from the group consisting of a thiol-modified cholesterol substituent, an amino-modified cholesterol substituent, a carboxy-modified cholesterol substituent, and an epoxy-modified cholesterol substituent.

In certain embodiments, the modified cholesterol comprises 3-mercapto-2-hydroxypropyl-cholesterol.

Also provided is a method comprising preparing the modified cholesterol by contacting a cholesterol with at least one reactant to provide the modified cholesterol having at least one substituent group, wherein the substituent group is a member selected from the group consisting of a thiol group, an amino group, a carboxy group, and an epoxy group.

In certain embodiments of the method, the cholesterol is treated with epihalohydrin to yield a glycidyl modified cholesterol and the glycidyl modified cholesterol is treated with a thiolating agent to yield a thiol modified cholesterol.

Also provided is process for preparing the modified polyurethane of the invention, the process comprising: reacting a steroid lipid with epihalohydrin to yield a glycidyl derivative of the steroid lipid; reacting the glycidyl derivative of the steroid lipid with a thiolating agent, thereby effecting opening of the glycidyl oxirane group and adding to said lipid molecule a thiol moiety having a protective group bound thereto; removing said protecting group to produce a thiol-substituted steroid lipid; reacting a polyurethane with a bi-functional linker comprising a thiol-reactive group, to yield an intermediate polyurethane having a thiol-reactive functional group wherein the thiol-reactive functional group is substituted on said urethane group nitrogen; reacting the thiol-substituted steroid lipid with the intermediate polyurethane having a thiol-reactive functional group to yield the modified polyurethane. In certain embodiments, the epihalohydrin is epibromohydrin.

In certain embodiments, the thiolating agent is selected from the group consisting of thiosulfate, thiourea, trityl-butylmercaptanes, tert-butylmercaptanes, thiocyanate, and thioalkanoic acids having 2-6 carbon atoms.

In certain embodiments, the thiolating agent is thioacetic acid.

In certain embodiments, the bi-functional linker is a dihaloalkane having 1-12 carbon atoms.

In certain embodiments, the bi-functional linker is 1,4-dibromobutane.

Also provided is a process of producing an implant, said process comprising: providing the modified polyurethane of the invention; forming an article from the modified polyurethane; contacting the article with cells to attach the cells to the lipid substituent and thereby attach the cells to the article to form the implant, provided that a substantial portion of the cells remains attached to the implant when exposed to a fluid-induced sheer stress.

In certain embodiments of the process, the lipid substituent is a member selected from the group consisting of a thiol-modified cholesterol substituent, an amino-modified cholesterol substituent, a carboxy-modified cholesterol substituent, and an epoxy-modified cholesterol substituent.

In certain embodiments of the process, the cells are endothelial cells or precursors of endothelial cells.

In certain embodiments of the process, the endothelial cells are bovine arterial endothelial cells or blood outgrowth endothelial cells.

Also provided is an implant produced by the process as described above. The non limiting examples of implant are an artificial heart; cardiac pacer leads; automatic implantable cardiodefibrilator leads; a prosthetic heart valve; a cardiopulmonary bypass membrane; a ventricular assist device; an annuloplasty ring; a dermal graft; a vascular graft; a vascular stent; cardiovascular stent; a structural stent; a catheter; a guide wire; a vascular shunt; a cardiovascular shunt; a dura mater graft; a cartilage graft; a cartilage implant; a pericardium graft; a ligament prosthesis; a tendon prosthesis; a urinary bladder prosthesis; a pledget; a suture; a permanently in-dwelling percutaneous device; an artificial joint; an artificial limb; a bionic construct; and a surgical patch.

Preferably in the implant, the cells are blood outgrowth endothelial cells.

Further provided is a method of treating a patient comprising providing the implant of the invention comprising modified polyurethane, wherein the implant is seeded with blood outgrowth endothelial cells.

Further provided is a method of treating or preventing a condition in a patient, said method comprising implanting in the patient an implant coated with cells, such that the cells are administered to the patient to treat or prevent the condition, wherein the cells are releasably attached to the implant by a lipid substituent pendant from at least one urethane nitrogen and/or at least one carbon atom of a polyurethane component of the implant. Non-limiting examples of condition are thrombosis and inflammatory cell interactions.

BRIEF DESCRIPTION OF SEVERAL VIEWS OF THE DRAWINGS

The patent or application file contains at least one drawing executed in color. Copies of this patent or patent application publication with color drawings will be provided by the Office upon request and payment of the necessary fee.

The invention will be described in conjunction with the following drawings in which like reference numerals designate like elements and wherein:

As shown in FIG. 11A, at temperatures at or below the glass transition phase ($T_g$), the storage modulus was greater for cholesterol modified polyurethane. As shown in FIG. 11A, the unmodified polyurethane had a lower $T_g$ and a higher melting temperature ($T_m$) compared to the cholesterol modified polyurethane. At 37° C. both storage modulus and Tan delta were similar for both polyurethane configurations.

FIGS. 13A-L demonstrate phase microscopy of bovine arterial endothelial cells (BAEC's) growing on glass (Figs. A-D), cholesterol modified polyurethane (FIGS. 13E-H), or unmodified polyurethane (FIGS. 13I-L) exposed to shear flow (25 dynes/cm$^2$) for 0 hours (FIGS. 13 F A, E, and I), 0.5 hours (FIGS. 13 H, F, and J), 1 hour (FIGS. 13 C, G, and K), or 2 hours (FIGS. 13 D, H, and L). Magnification was 200×.

FIGS. 14A-L demonstrate phase microscopy of bovine blood outgrowth endothelial cells (BOEC's) growing on glass (Figs. A, B, C, and D), cholesterol modified Tecothane (FIGS. 14 E-H), or unmodified Tecothane (FIGS. 14 I-L), and exposed to shear flow (25 dynes/cm$^2$) for 0 (FIGS. 14 A, E, I), 0.5 (FIGS. 14 B, F, J), 1 (Figs. C, G, K), and 2 hours (FIGS. 14 D, H, L). Magnification=200×.

FIG. 14L). In contrast only 4.56±0.85% of BOEC's seeded on unmodified polyurethane were retained after 2 hours. Data are mean±SEM. *$_1$p=0.04; *$_2$p=0.01; *$_3$p=0.001; †$_1$p=0.006; †$_2$p=0.01; †$_3$p=0.001

FIGS. 17A and B demonstrate high shear (2 hours at 25 dyne/cm$^2$) adhesion on cholesterol modified but not on unmodified with endothelial precursor cells (BOEC), wherein FIG. 17A is a block diagram and FIG. 17B is a micrograph (Tec is unmodified polyurethane, glass and Chol-tec is modified polyurethane).

FIGS. 18 A and B, demonstrate a higher shear adhesion on cholesterol modified but not on unmodified with endothelial precursor cells (BOEC), used such as 75 dynes/cm$^2$ for 2 hours, which is significant since it is typical heart valve level shear force. Also shown are the first results we have demonstrating retention of seeded endothelial cells on cholesterol modified polyurethane in blood stream implants.

DETAILED DESCRIPTION OF THE INVENTION

Figure 1:
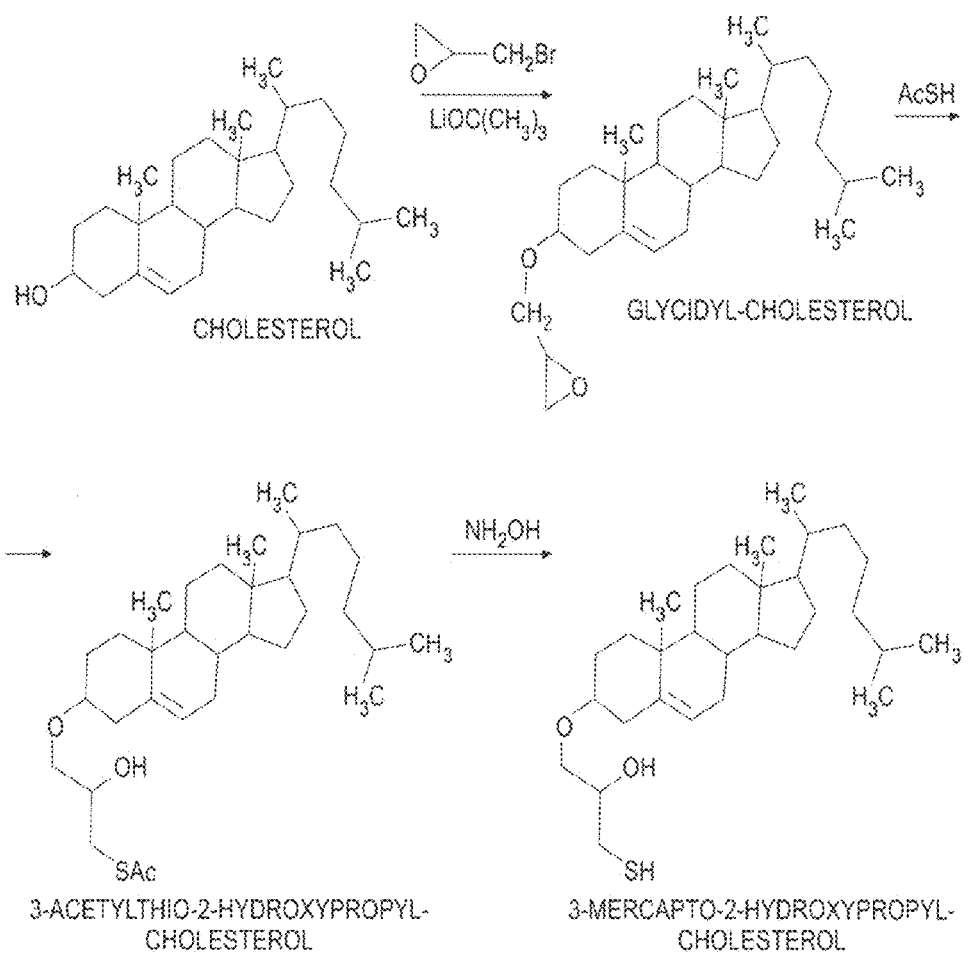
FIG. 1 is a reaction scheme for modification of cholesterol with a thiol-containing substituent group by sequential reaction with epihalohydrin, thioacetic acid and hydroxylamine.

The present invention is based upon the discovery of modified polyurethanes that have lipid substituents pendant from at least one nitrogen and/or at least one carbon atom of the polyurethane and methods of making such polyurethanes. The inventors have discovered that lipid-modified polyurethane and especially steroid lipid-modified polyurethane allows for adhesion of cells which remain associated with the modified polyurethane during exposure to high sheer force. Unexpectedly, the inventors have discovered that modified polyurethane is less prone to degradative oxidation than a polyurethane. Accordingly, the invention provides modified polyurethane comprising a lipid substituent pendant from at least one urethane nitrogen and/or at least one carbon atom of the modified polyurethane.

Endothelialization of synthetic surfaces has been challenging with limited success thus far. The inventors discovered that covalent attachment of cholesterol to polyurethane via the urethane nitrogen groups would create a high affinity surface for attachment and adhesion of endothelial cells. Cholesterol was covalently bound to the polyether polyurethane, Tecothane®, by first derivatizing the polyurethane nitrogen groups with bromo-alkyl side chains, followed by reacting mercapto-cholesterol to the bromoalkyl sites. Cholesterol modified polyurethane demonstrated a qualitatively smoother surface per atomic force microscopy than nonmodified and increased surface energy (contact angle measurements) compared to unmodified polyurethane. Cell attachment assays showed a significantly higher rate of attachment of bovine arterial endothelial cells (BAEC's) (p=0.0003) after 45 minutes of seeding on cholesterol modified polyurethane versus unmodified polyurethane. BAEC's cultivated on cholesterol-modified Tecothane® showed significantly greater levels of cell retention compared to unmodified Tecothane® when exposed to arterial level shear stress for 2 hours (25 dynes/cm$^2$) with 90.0±6.23% cells remaining adherent compared to unmodified polyurethane, 41.4±11.7%, p=0.0070. Furthermore, ovine endothelial precursors, obtained as blood outgrowth endothelial cells (BOEC's), were seeded on cholesterol modified polyurethane and exposed to 25 dynes/cm$^2$ shear conditions for 2 hours, with the retention of 90.30±3.25% of seeded cells versus unmodified polyurethane, that retained only 4.56±0.85% (p<0.001). It is concluded that covalently linking cholesterol to polyurethane results in improved material properties that permit increased endothelial cell retention compared to unmodified polyurethane.

As used herein, each of the following terms has the meaning associated with it in this section, absent an express indication to the contrary.

The articles "a" and "an" are used herein to refer to one or to more than one (i.e. to at least one) of the grammatical object of the article. By way of example, "an element" means one element or more than one element.

"Implantation," and grammatical forms thereof, refers to the process of contacting a device with a tissue of an animal in vivo wherein the contact is intended to continue for a period of hours, days, weeks, months, or years without substantial degradation of the device. Such contact includes, for example, grafting or adhering the device to or within a tissue of the animal and depositing the device within an orifice, cavity, incision, or other natural or artificially-created void in the body of the animal.

An "implantable" device is one which is adapted for permanent or temporary insertion into or application against a tissue of an animal such as a human. Examples of implantable devices or components include, but are not limited to, an artificial heart; cardiac pacer leads; automatic implantable cardiodefibrilator leads; a prosthetic heart valve; a cardiopulmonary bypass membrane; a ventricular assist device; an annuloplasty ring; a dermal graft; a vascular graft; a vascular, cardiovascular, or structural stent; a catheter; a guide wire; a vascular or cardiovascular shunt; a dura mater graft; a cartilage graft; a cartilage implant; a pericardium graft; a ligament prosthesis; a tendon prosthesis; a urinary bladder prosthesis; a pledget; a suture; a permanently in-dwelling percutaneous device; an artificial joint; an artificial limb; a bionic construct (i.e. one of the aforementioned devices or components comprising a microprocessor or other electronic component); and a surgical patch.

An "oxirane" ring or group is also known as an epoxy ring or group.

A "thiol-reactive functional group" is a moiety capable of reacting with thiol group (—SH) such that a covalent bond is formed between an atom of the compound containing the thiol-reactive functional group and the sulfur atom of the thiol group.

A "thiolating agent" is any agent, such as a thiol nucleophile, that introduces a thiol group or a sulfide which is readily transformed to a thiol by, for example, hydrolysis or reduction. Examples of thiolating reagents include, without limitation, thiosulfate, thiourea, trityl- and tert-butylmercaptans, thiocyanate, and thioalkanoic acids such as thioacetic acid. Reagents such as thiosulfate, thiourea, trityl- and tert-butylmercaptans, and thiocyanate require further treatment by, for example, hydrolysis or reduction of the resultant sulfur-containing compound to obtain the desired thiol group. In a preferred embodiment, the thiolating agent is thioacetic acid.

The term "alkyl" refers to a hydrocarbon containing from 1 to 12 carbon atoms unless otherwise defined. An alkyl is an optionally substituted straight, branched or cyclic saturated hydrocarbon group. When substituted, alkyl groups may be substituted at any available point of attachment. When the alkyl group is said to be substituted with an alkyl group, this is used interchangeably with "branched alkyl group". Exemplary unsubstituted groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as $CCl_3$, or $CF_3$), alkoxy, alkylthio, hydroxy, carboxy (—COOH), carbonyl (—C(=O)), epoxy, alkyloxycarbonyl (—C(=O)—OR), alkylcarbonyloxy (—OC(=O)—R), amino (—$NH_2$), carbamoyl ($NH_2C$(=O)— or NHRC(=O)—), urea (—NH—CONH$_2$), alkylurea (—NHCONHR) or thiol (—SH), wherein R in the aforementioned substituents represents an alkyl radical. Alkyl groups (moieties) as defined herein may also comprise one or more carbon to carbon double bonds or one or more carbon to carbon triple bonds. Alkyl groups may also be interrupted with at least one oxygen, nitrogen, or sulfur atom.

The term "biomaterial" as used herein denotes any synthetic biocompatible polymeric material which is known, or is hereafter developed, as being suitable for in-dwelling uses in the body of a living being, i.e., which is biologically inert and physiological acceptable, non-toxic, and insoluble in the environment of use.

Polyurethanes

In accordance with the teachings of this invention, the polyurethane has at least one pendant thiol substituent which is either thiol or protected thiol group or a mixture of both.

The term "polyurethane," as used herein, is a polymer that comprises repeating units having a urethane group in the polymer backbone. Such polymers include, for example, polyurethane homopolymers, block co-polymers comprising at least one polyurethane block, and polymer blends comprising such homopolymers and block co-polymers. Illustrative polyurethanes include but are not limited to F2000 PEU, which is a medical grade polyether-urethane prepared from 4,4-methylenebis(phenylisocyanate), polytetramethyleneoxide (MW ca. 1,000 g/mol), and 1,4-butanediol as a chain extender (Sulzer Carbomedics, Inc.; Austin, Tex.); BIO-SPAN™, which is a medical grade polyurethane-urea and BIONATE™ 80A, which is a medical grade polycarbonate-urethane (both from Polymer Technology Group Medical, LLC; Berkeley, Calif.); and TECOTHANE™ TT-1074A, which is a medical grade polyether-urethane (Thermedics, Inc.; Woburn, Mass.). Such polymers include, for example, both polyether polyurethanes and polyester polyurethanes which may be in the form of homopolymers, block co-polymers comprising at least one polyurethane block, and polymer blends comprising such homopolymers and block co-polymers.

A chemical substituent is "pendant" from a backbone of a polymer if it is bound to an atom of a monomeric unit of the polymer. In this context, the substituent can be pending from a carbon atom of a backbone, a carbon atom connected to a carbon atom of the backbone by a chain extender, or a urethane nitrogen of the backbone of the polyurethane.

A "urethane group" is a chemical structure which is part of the backbone of a polymer and which has the following structure:

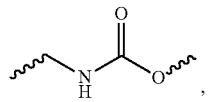

The "backbone" of a polymer is the collection of atoms and chemical bonds therebetween which link the repeating units of the polymer to one another.

A chemical substituent is "pendant" from the backbone of a polymer if it is attached to an atom of a monomeric unit of the polymer, either directly or indirectly, e.g. through a linker moiety.

Polyurethanes suitable for the instant invention may be obtained commercially (such as Tecothane; Thermedics Inc., Woburn, Mass.). Preferably, the polyurethanes are resistant to degradation, suitable for implantation into an animal, and have a chemically accessible nitrogen of the urethane groups.

Alternatively, polyurethanes can be made by condensing a diisocyanate (OCN-A-CNO) with a diol (HO—X—OH), with two or more diols having different structures, or with both a diol and a diamine. It is understood that the proportion of end groups corresponding to the diisocyanate and the diol can be controlled by using an excess of the desired end group. For example, if a reaction is performed in the presence of an excess of the diisocyanate, then the resulting polyurethane will have isocyanate (—NCO) groups at each end.

Depending on the identity of the reaction products used to from them, polyurethanes can behave as elastomers or as rigid, hard thermosets. If the diisocyanate in the synthesis reaction is, for example, 4,4'-methylenebis(phenylisocyanate), then the resultant polyurethane will be relatively inflexible. If the diol in the synthesis reaction is, for example, polytetramethyleneoxide (i.e., HO—($CH_2CH_2CH_2CH_2$O)$_k$—H, wherein, e.g., k is about 10 to 30), then the resultant polyurethane will be relatively flexible. Methods of selecting polyurethane precursors which will yield a polyurethane having hard and soft segments which confer a desired property (e.g., flexibility, elastomericity, etc.) to the polyurethane are well known in the art.

Methods of making segmented polyurethanes are also known in the art. In these methods, one or more types of polyurethane precursors (OCN—P—NCO) are reacted with a chain extending compound (HZ-Y-ZH) to yield a segmented polyurethane. By varying the proportions of different types of polyurethane precursors, their end groups, the identity of the chain extender, and the like, the composition of polyurethane segments in the segmented polymer can be controlled, as is known in the art. Medical grade segmented polyurethanes are usually prepared by condensing a diisocyanate with a polymeric diol having a molecular weight of about 1,000 to 3,000 (e.g., polytetramethyleneoxide for polyether-urethanes or polycarbonatediols for polycarbonate-urethanes) in order to form a polyurethane precursor which is subsequently reacted with an approximately equivalent amount of a chain extender (e.g., a diol such as 1,4-butanediol or a diamine such as a mixture of diaminocyclohexane isomers).

The lipid molecules which may be used in the practice of this invention are preferably lipids common to cellular membranes such as, without limitation, phospholipids (e.g., phophatidylcholine, sphiongomyelin, phophatidylserine, and phophatidylethanolamine), steroid lipids (i.e. lipids containing a steroid ring structure and a nonpolar hydrocarbon tail), glycolipids, and derivatives thereof. Steroid lipids (e.g. cholesterol and derivatives thereof) are preferred for immobilization on the polyurethane as the steroid ring is nonbiodegradable. The lipids attached to the polyurethane may all be the same or more than one type of lipid may be attached, if desired. Additionally, membrane proteins may be added exogenously and allowed to interact with the lipids immobilized on the polyurethane to organize pseudomembranes.

The lipid molecule may be derivatized for attachment of a thiol group. This may be conveniently carried out by reacting the lipid molecule with an oxirane-containing compound, preferably an epihalohydrin. Suitable epihalohydrins which can be employed for this purpose include, for example, epichlorohydrin, epibromohydrin, epiiodohydrin, methylepichlorohydrin, methylepibromohydrin, methylepiiodohydrin, ethylepichlorohydrin, ethylepibromohydrin, ethylepiiodohydrin, propylepichlorohydrin, propylepibromohydrin, propylepiiodohydrin, butylepichlorohydrin, butylepibromohydrin, butylepiiodohydrin, and the like.

The thiol group may be thereafter introduced by reaction between the oxirane-containing lipid derivative and the thiolating agent. Other methods (e.g., the replacement of the hydroxy group with a thiol function via cholesteryl tosylate and thiuronium salt) can also be used to provide the lipid with a highly reactive thiol group. Alternatively, modified cholesterols containing a reactive thiol group, such as thiocholesterol, are also commercially available (Sigma, St. Louis, Mo.).

The linker moiety used to attach a lipid to a polyurethane in practicing the present invention is preferably the residue of a compound which comprises an alkyl moiety that joins at least one reactive group that is a thiol-reactive functional group and at least one reactive group capable of attachment to the urethane group nitrogen of the polyurethane. Preferably, the linker moiety is nondegradable. The linker moiety may be derived from a dihaloalkane having from 1 to about 12 carbon atoms with the halogens substituted on the terminal carbon atoms, such as 1,4-di bromobutane; 1,3-dibromopropane; 1,5-dibromopentane; and 1,6-dibromohexane. The compound providing the linker moiety may also comprise a halogen and an epoxy group thereby providing the polymer with pendant glycidyl groups which may be readily reacted with thiolated lipids (see, for example, the reaction of polyurethanes with epibromohydrin in Alferiev, L. S., J. Polym. Sci., Part A: Polym. Chem., 2002, 40:4378-4385). The linker moiety may also be interrupted with at least one sulfur, nitrogen, or sulfur atom and further comprise substituents such as, but not limited to, hydroxy groups and carbonyl groups. Reaction between polyurethane and the multifunctional linker reagent is also described in detail in copending U.S. patent application entitled U.S. patent application Ser. No. 10/672,893 filed on Sep. 26, 2003, entitled NOVEL THIOL ACTIVATION OF POLYURETHANES AND METHODS OF MAKING THE SAME and U.S. patent application Ser. No. 10/672,892, filed on Sep. 26, 2003, entitled DERIVATIZED POLYURETHANE COMPOSITIONS WHICH EXHIBIT ENHANCED STABILITY IN BIOLOGICAL SYSTEMS AND METHODS OF MAKING THE SAME (this application is a continuation-in-part of application Ser. No. 09/985,316, filed on Nov. 2, 2001, which is a continuation of application Ser. No. 09/620,857, filed on Jul. 21, 2000, now U.S. Pat. No. 6,320,011, issued on Nov. 20, 2001 which are incorporated herein in their entireties.

Figure 7:
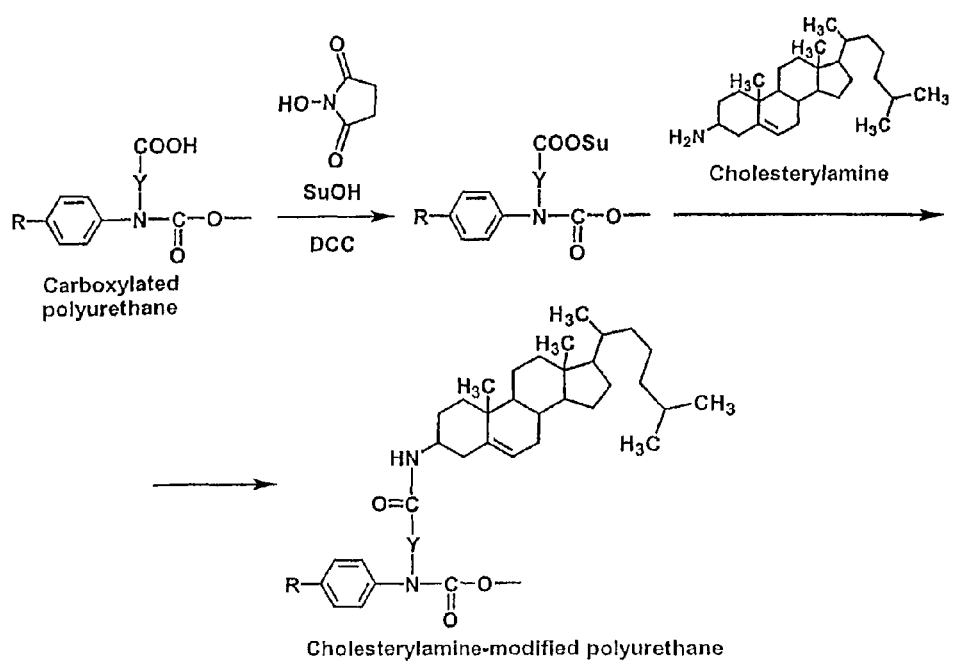
FIG. 7 is a reaction scheme for the preparation of a cholesterol-modified polyurethane from a carboxylated polyurethane and an amino-substituted cholesterol through the use of N-hydroxysuccinimide esterification. Y is a linker moiety as described further herein.
Figure 8:
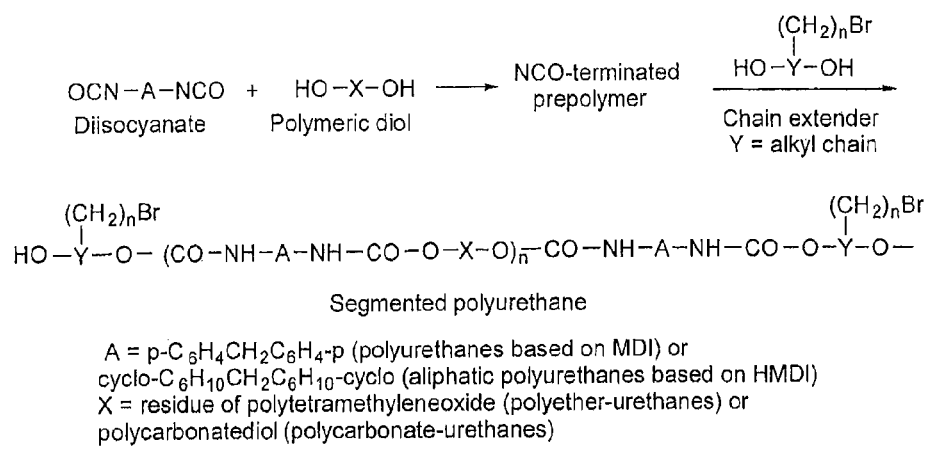
FIG. 8 is a reaction scheme depicting a synthesis of a polyurethane using chain extenders which are pre-modified with reactive bromoalkyl groups. Polyurethane precursors terminated with isocyanate groups are reacted with bromoalkyl-containing diols as chain extenders. In this reaction, modification of carbon atoms of the backbone of polyurethane and not urethane nitrogen is obtained. Next, the pendant bromoalkyl groups can be used for further derivatization with, for example thiolated cholesterol as shown in FIG. 2 thus resulting in modification of carbon atoms of the backbone.

Other methods of covalently binding a lipid to a polyurethane by use of a linker moiety that is different than the dihaloalkanes described above would be readily apparent to a skilled artisan. For example, polyurethane may be modified with pendant carboxy groups via N-hydroxysuccinimide esterification and subsequently reacted with an aminated lipid. More specifically, polyurethanes can be provided with pendant carboxy groups (as described in U.S. Pat. No. 6,320,011) either by direct carboxyalkylation (see, e.g., Example 2 of U.S. Pat. No. 6,320,011) or by carboxyl derivatization of pendant omega-bromoalkyl groups (see, e.g., Example 10 of U.S. Pat. No. 6,320,011). The carboxy groups can then be activated via N-hydroxysuccinimide esterification (U.S. Pat. No. 6,320,011) and reacted with an aminated lipid such as cholesterylamine (Kan, C. C., et al., Biochemistry 1992, 31(6), 1866-74). The reaction scheme is exemplified in FIG. 7.

The chemical reactions utilized to make the polymer material of the invention are easily performed. In the preferred approach, a lipid molecule is reacted with an oxirane-containing compound in such a manner that the oxirane-containing compound is covalently bound to the lipid. The epoxy ring substituent of the lipid is subsequently opened by a reaction with an epoxy-reactive thiolating agent, thereby yielding a thiol-substituted lipid, in which the thiol group is optionally protected. The ring opening results in formation of a covalent bond between the epoxy-reactive thiolating agent and an atom of the epoxy ring. If present, the protective group on the thiol group is then removed.

Additionally, a polyurethane biomaterial is modified to contain a thiol-reactive functional group. Such a functional group may be added directly to the nitrogen atom of the urethane group or, preferably, through a linker moiety. Subsequently, the thiol-substituted lipid molecule is reacted with the polyurethane containing a thiol-reactive functional group, thereby yielding the desired lipid-modified polyurethane.

Implantation devices comprising the lipid modified polyurethanes of the invention are advantageously seeded with cells prior to implantation of the device. Typically, the cells are autologous endothelial cells.

There are multiple techniques known in the art for the seeding of selected cells to an implantation device (see, for example, U.S. Pat. Nos. 5,674,722; 5,785,965; and 5,766,584). Typically, the implantation device is incubated in vitro, optionally with rotation, to allow the binding of the endothelial cells to the surface of the device. After several hours or days of culture, the device may be implanted into the host. Alternatively, the endothelial cells may be mixed with blood prior to application onto the implantation device.

More specifically, the number of cells deposited on the device may be between about $10^3$ cells/$cm^2$ and $10^{12}$ cells/$cm^2$ of device surface, typically about $5 \times 10^5$ cells/$cm^2$. The cells are deposited in any convenient sterile medium, e.g. phosphate buffered saline (PBS), normal saline, M199, Dulbecco's Modified Eagles Medium (DMEM), and the like. The volume of medium will be sufficient to resuspend the cells, generally ranging from about 1 to 25 ml of medium.

After deposition, the prosthesis may be implanted immediately into the recipient or more preferably be maintained in culture for a period of time. The culture conditions are conventional for endothelial cells, for example, the prosthesis may be deposited in a plate or well containing medium and fetal calf serum, then incubated at 37° C. The culturing medium may be changed at least every 2-3 days, usually daily. The prosthesis will generally be maintained in culture for not more than about three weeks, usually for not more than about two weeks, and preferably will be used within about one week.

Cells employed for seeding on the implantable device may be obtained by any method known in the art. Cells may be obtained at the time of the implantation procedure using standard biopsy techniques, whether the procedure is angioplasty, open field surgery or for diagnostic purposes. The cells may also be dissociated with collagenase or trypsin and seeded directly into a matrix as exemplified below for immediate implantation or for culturing in vitro as required to generate the number of cells to be implanted. Specifically, cells may be isolated by standard methods described in, for example, Gimbrone, M. (1976) Progress Hemostasis and Thrombosis 3:1-28 and U.S. Pat. No. 5,131,907.

Lithium-tert-butoxide, Histopaque-1077, sodium hydroxide, cholesterol, tetrahydro-fluorane (THF) were purchased from Sigma (St. Louis, Mo.). Tecothane® TT1074A, an aromatic polyether polyurethane, was obtained from Thermedics Inc. (Woburn, Mass.), purified and characterized by $^1$H NMR as reported previously[3]. N,N-dimethylacetamide (DMAC) was purchased from Aldrich Chemicals. 4',6-Diamidino-2-phenylindole (DAPI) fluorescent stain was purchased from Vector Labs (Burlingame, Calif.). Glass microscope slides were obtained from Fisher Scientific (Pittsburgh, Pa.). EGM-2 culture media was purchased from Clonetics (San Diego, Calif.). Dulbecco's modification of Eagle's medium (DMEM) was purchased from Cellgro (Herndon, Va.) and Trypsin/EDTA was acquired from Gibco (Grand Island, N.Y.).

Bovine aortas, obtained from a local abattoir, were cleaned of excess tissue and cut longitudinally. A warmed solution of DMEM (supplemented with 10% Fetal Bovine Serum, non-essential amino acids and penicillin streptomycin) containing collagenase (2.5 mg/ml, Gibco) was pipetted onto, up, and back onto to the inside of the aorta for 2-5 minutes. The released cells in suspension were collected, centrifuged, and resuspended in culture media. The cell suspension was put through a 300 mesh sieve and the top layer containing cell clusters was collected and plated on tissue culture plates. BAEC's were maintained (37° C., 5% $CO_2$) in DMEM supplemented with 10% FBS and penicillin streptomycin. BAEC's used in this study were between passages 5-12.

Sheep blood outgrowth endothelial cells (BOEC's) were prepared from freshly drawn peripheral blood using a previously published method[7] and all procedures and animal husbandry were in compliance with NIH standards pertaining to the care and use of laboratory animals as approved by the IACUC of the University of Minnesota. Briefly, heparinized peripheral blood (100 mls) was collected from a juvenile sheep by venipuncture. Mononuclear cells were isolated from blood using Histopaque-1077, according to the manufacturer's instructions. The buffy coat was collected, washed with HBSS and resuspended in EGM-2 culture media. The resuspended cells were seeded onto a tissue culture dish precoated with acetic acid denatured collagen. The culture media was changed every other day and the cells were subcultured using Trypsin/EDTA. Endothelial cell phenotype was confirmed using uptake of acetylated LDL, immunocytochemistry for P1H12 and VE-cadeherin[7-9].

Preparation of Cholesterol Modified Tecothane®

Figure 2:
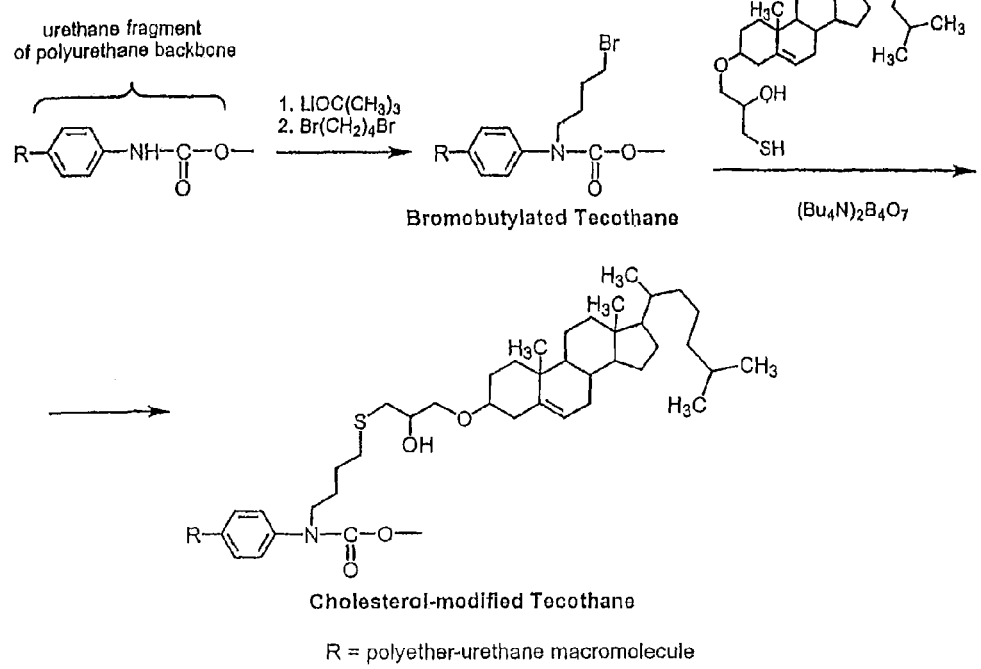
FIG. 2 is a reaction scheme for the preparation of a cholesterol-modified polyurethane from a polyurethane having a thiol-reactive functional group and a thiol-substituted cholesterol.

A schematic diagram of the reactions used for covalent binding of cholesterol to the urethane hard segments by the reaction of bromobutylated Tecothane® with 2-hydroxy-3-β-cholesteryloxypropanethiol is presented in FIGS. 1 and 2. Glycidyl cholesterol (FIG. 1) was synthesized by dissolving cholesterol in DMAc under a flow of dry argon and adding 1 M lithium tert-butoxide in hexanes. After cooling to 5° C., freshly distilled epibromohydrin was added and the mixture was stirred at 3-5° C. for 2 hours and allowed to slowly come to room temperature (21-23° C.) where it was incubated for an additional hour. The reaction mixture was diluted with 0.5% aqueous $KHCO_3$ and extracted with three administrations of n-heptane. The combined organic layers were dried over $Na_2SO_4$. After filtration from the desiccant, the solvent was removed in vacuo and the residue was purified by flash-chromatography on silica gel employing elution with hexane, hexane/toluene (1:1 mixture), and toluene. The fractions containing pure glycidyl cholesterol were pooled and dried in vacuo until crystallization occurred. Purity was confirmed with $^1$H NMR (data not shown).

Freshly distilled thioacetic acid was dissolved in DMAc under argon protection and cooled to −10° C. A 0.35 M freshly prepared solution of $(Bu_4N)_2B_4O_7$ in DMAc was added. Glycidyl cholesterol, from above, was dissolved in DMAc and added to the resulting solution. The mixture was allowed to react for 2 hours at 0° C. and then poured into ice-cold water. The product was extracted with decreasing volumes of n-heptane. The organic layers were dried at 4° C. over $Na_2SO_4$, filtered and dried in vacuo. Crude 1-acetylthio-3-β-cholesteryloxy-2-propanol was dissolved in THF and mixed with a 2.7 M solution of $NH_2OH$ in 2-propanol (100 mmol) under argon. The mixture was allowed to react at room temperature for 5 hours and diluted with 1.2% aqueous $H_3PO_4$. Organic solvents were removed in vacuo below 30° C. together with a part of water. The resultant solid precipitate was filtered off, thoroughly washed with water and dried in vacuo. Crude 2-hydroxy-3-β-cholesteryloxypropanethiol was purified by flash-chromatography (silica gel, hexane then hexane-ethyl acetate, 10:1), and analyzed for purity via $^1$H NMR.

Figure 9:
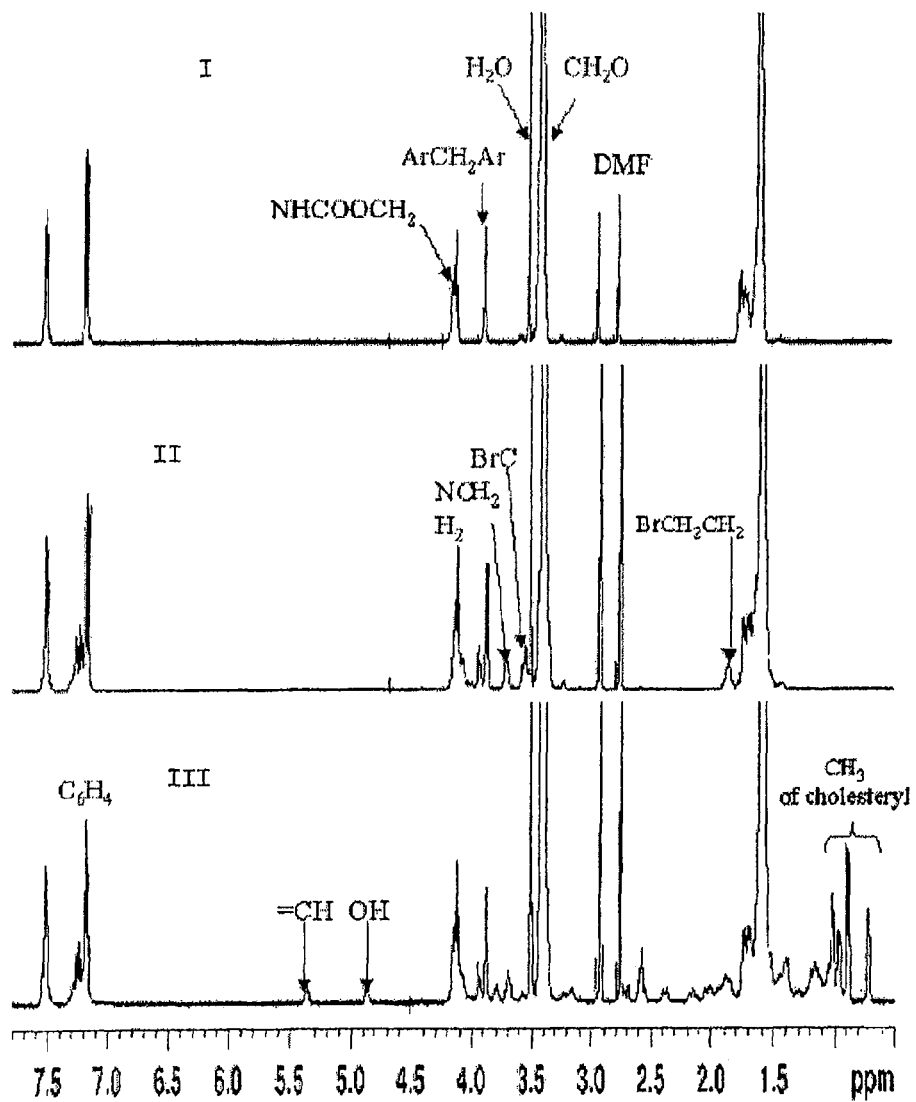
FIG. 9 (I II III) is a $^1$H NMR spectrum confirming covalent attachment of cholesterol to a polyether urethane. The urethane fragment of Tecothane® was bromobutylated and then reacted with, the above mentioned thiolated cholesterol as shown in FIGS. 1 and 2. $^1$H NMR spectrum of non-modified Tecothane® is shown for reference (I). Signals of pendant bromobutyl groups are clearly noticeable in the NMR spectrum (II). After covalent attachment of cholesterol, new NMR signals appear in the spectrum of the polymer as indicated (III). Alkylation of urethane nitrogens also cause pronounced changes in the region of aromatic protons (see II and III, δ=7.1-7.5 ppm).

Cholesterol modified Tecothane® (FIG. 2) was bromobutylated as described previously[1], and characterized by $^1$H NMR (FIG. 9). The results revealed that about 20% of urethane segments were modified with pendant 4-bromobutyl groups (FIG. 9). The polymer was dissolved in DMAc under argon and cooled to −2° C. A solution of 2-hydroxy-3-β-cholesteryloxypropanethiol from above, in DMAc and a freshly prepared 0.24 M DMAc-solution of $(Bu_4N)_2B_4O_7$ were added. The mixture was stirred at −1 to 1° C. for one hour and acidified with acetic acid (10.5 mmol). The reaction solution was then filtered and the polymer was precipitated with cold (−12° C.) methanol. The precipitate was washed with methanol alternating with 2-propanol and stirred constantly with large amounts of 2-propanol, methanol, and water and dried under 0.05 mm Hg conditions. $^1$H NMR (see FIG. 9) analysis of this polymer indicated covalent attachment of cholesterol to about 20% of the urethane segments via noncleavable, sulfide bonds corresponding to approximately 0.4 mmol of pendant cholesterol moieties per gram of polymer.

Cholesterol modified Tecothane® was highly soluble in tetrahydrofuran (THF), comparable to unmodified Tecothane®. For solvent casting films, Tecothane®-cholesterol (5.6 gm/100 ml in THF) and unmodified Tecothane® (5.2 gm/100 ml in THF) thin films were solvent cast onto Teflon-foil coated petri dishes, and were air dryed in a fume hood. Film thickness ranged from 159 to 220 microns. These thin films were used in all of the material and cell culture studies described, and where relevant differences were noted between the air-dried side and the surface prepared in contact with Teflon. Methodology for preparing polyurethane films on glass slides for shear stress studies is described below.

Material properties of the modified and unmodified polyurethane films were assessed using a Perkin Elmer (Wellesley, Mass.) DMA 7. Samples were cooled to −68° C. and heated to 120° C. at a rate of 3° C. min$^{-1}$. Data measuring material elasticity (Storage Modulus) and mechanical loss factor (Tan Delta), which reflects differences in calorimetry parameters between materials, at a test frequency of 10 Hz were analyzed using the Pyris software package (Perkin Elmer).

The water contact angle on unmodified or cholesterol modified Tecothane was measured on a custom built imaging-goniometer system using established methodology[10], and was recorded as the average of 8 measurements of each sample. The sessile drops were immediately visualized using a CCD camera (Edmund Scientific Co., Barrington, N.J.) and contact angle measurements were analyzed using Scion Image analysis software package (Scion Inc., Frederick, Md.).

Films composed of Tecothane or cholesterol-modified Tecothane were cut into 1 cm square sections (thickness≈150 um) and placed in the bottom of a 24 well plate. BAEC's were trypsinized and added to each well (10,000 cells/well). Cells were incubated at 37° C. At fifteen-minute intervals, the polyurethane films were gently washed with PBS and adherent cells were fixed with cold 4% paraformaldehyde. Cells were quantified by staining with DAPI, a fluorescent, nuclei specific stain, and counted under 200× magnification with the appropriate fluorescent filter set using a Nikon TE-300 (Nikon Inc., Tokyo, Japan) inverted microscope.

Glass microscope slides (73×38×1 mm) were treated for 1 hour with 2 M NaOH[11], washed with distilled water, autoclaved, and inserted into Teflon coated casts with identical dimensions. Tecothane or cholesterol modified Tecothane was dissolved in THF at a final concentration of 20 mg/ml and 3 mls was added to each slide. The coated slides were loosely covered with foil and the THF solvent was evaporated overnight at room temperature. The uniform thickness of the polyurethane coating was 10 μm. Trypsinized BAEC's or BOEC's were suspended in DMEM or EGM media respectively, supplemented with 10% fetal calf serum and penicillin-streptomycin (100 μg/ml), and were seeded directly on the polyurethane-coated slides. Cells were grown until confluence and then the glass slides were inserted into a parallel plate shear chamber forming a flow channel (264 μm height × 15.4 mm width 58 mm length) between the monolayer and the fabricated polycarbonate plate[11]. Non-pulsatile, laminar shear flow utilized serum supplemented medium at 37° C., and was controlled by maintaining the flow rate of a peristaltic pump at 43 ml/min for glass slides and 40 ml/min for polyurethane coated slides. Shear stress ($T_w$) was calculated by the following equation $$T_w = \frac{6\mu Q}{w(x)^2}$$

where μ is the media viscosity, w is the width of the flow chamber, x is the height of the flow chamber, and Q is the flow rate. A shear stress of 25 dynes/cm$^2$ was applied, approximating systemic arterial shear conditions. After exposure to shear for set times of 30, 60 and 120 minutes, the slides were detached from the chamber, washed in PBS for 10 minutes, and then fixed in 4% paraformaldehyde. Cells were stained with DAPI and quantified as the number of DAPI positive cells in a minimum of 9 random, 200× fields/slide.

Cholesterol-modified and unmodified polyurethane films were imaged using a Model 3100 multi-mode atomic force microscope (Digital Instruments, Santa Barbara, Calif.). Imaging was performed in the intermittent non contact (tapping) mode, using oscillating linear Si tips at resonance frequency of 315.81 KHz. Each data scan was collected over a 10 □m$^2$ area at a scanning frequency of 0.50 Hz. The 2D and 3D morphology, as well as surface roughness data were collected and analyzed using the Nanoscope version 4.43r6 software package (Digital Instruments, Santa Barbara, Calif.).

Fourier Transform Infrared Spectroscopy-Attenuated Total Reflectance

Fourier transform infrared spectra of the samples were measured by attenuated total reflectance spectroscopy (FTIR-ATR) using a Nicolet 5-Protege 460 spectrophotometer E.S.P. (Nicolet, Madison, Wis.). All spectra were the result of 200 scans collected at a resolution of 2 cm$^{-1}$ at a 45° angle of incidence. All spectra were recorded under identical conditions and adjusted for atmospheric water vapor and carbon dioxide transmittance by subtraction of the appropriate reference spectrum using the Omnic software package (Nicolet). Polyurethane film thickness was approximately 150 μm.

Data were calculated as means standard error (SE). Student's t-test was used to determine the significance of differences. Statistical significance was noted with p≦0.05.

Figure 10:
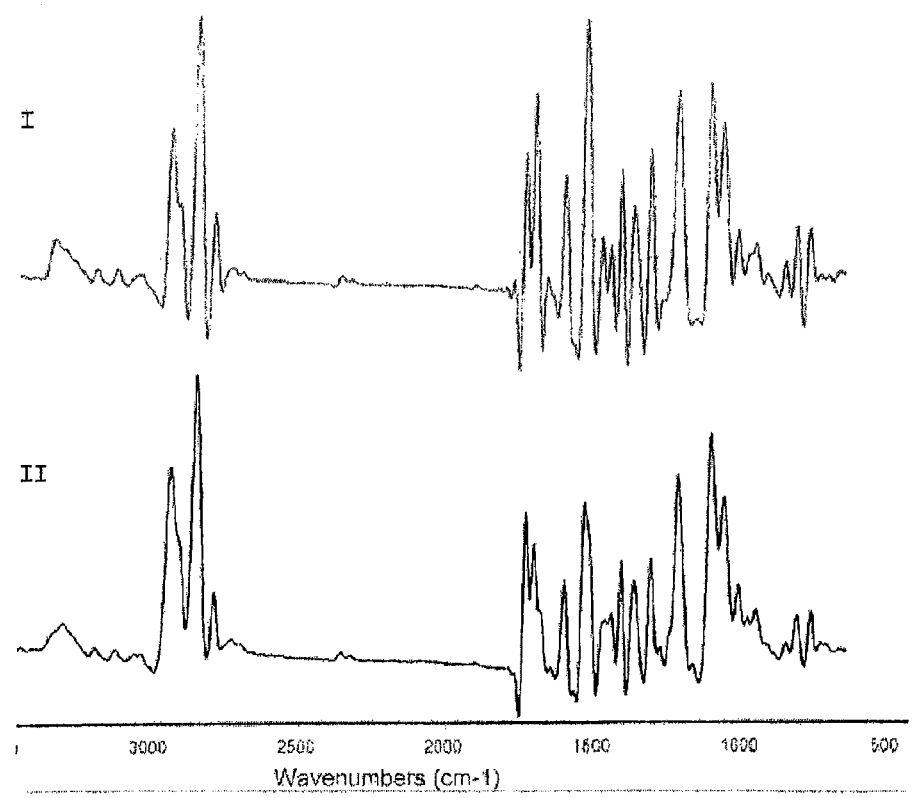
FIG. 10 shows Fourier Transform Infrared Spectra (FTIR) for air exposed sides of unmodified Tecothane® (I) and cholesterol derivatized modified Tecothane® (II). Results demonstrating peak shifts largely corresponding to changes in the nitrogen groups of the urethane hard segment.

FTIR analysis (FIG. 10) was used to compare the surface chemistry of the cholesterol modified and unmodified polyurethane on both the air exposed and non-air exposed sides of the polyurethane. The FTIR spectra for the air exposed surfaces (FIG. 10) were identical to the non-air exposed sides of their respective films (data not shown). The peak assignment as shown in Table 1 revealed peak shifts in the cholesterol modified Tecothane® at 3302, 1680, 743 and 717 cm$^{-1}$. The peak shift at 3329 in the unmodified polyurethane and the appearance of the displaced peak at 3302 most likely represent a shift in the hydrogen bonding between the nitrogen and the hydrogen in the hard segment. This bond was the target of the bromobutylation step and would thus be altered in the cholesterol containing polyurethane[1,3,12]. Likewise the appearance of peaks at 1680, 743 and 717 in the cholesterol-modified polyurethane probably represents the carboxyl bond in cholesterol (1680) and the sulfur (743 and 717) of the pendant molecules. Thus, these data show the presence of cholesterol moieties at or near the polyurethane surface.

Figure 11A:
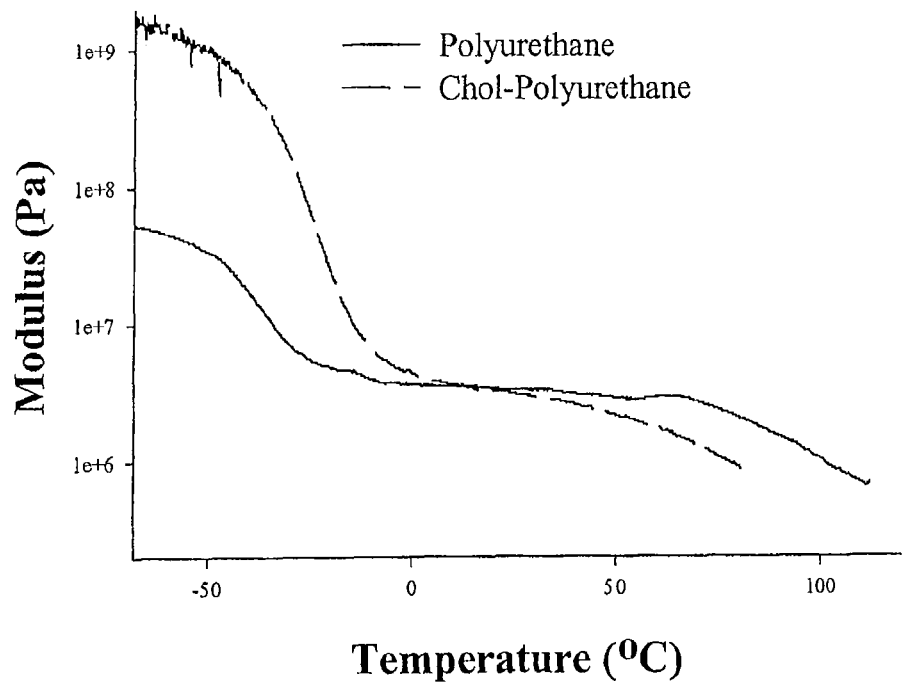
FIGS. 11A and 11B are graphic presentations of dynamic mechanical analysis showing representative runs, wherein FIG. 11A indicates the storage modulus (Pa=Pascal's) and the FIG. 11B indicates the Tan delta measurements of unmodified and cholesterol modified Tecothane.
Figure 11B:
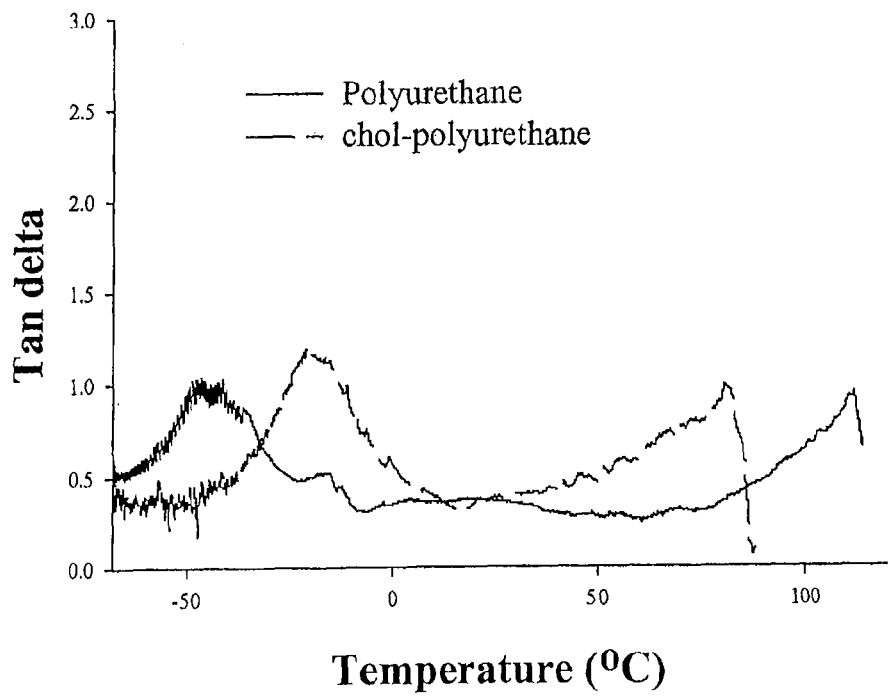

To determine the changes in material properties resulting from appending cholesterol moieties to the urethane hard segment of Tecothane®, DMA was used to compare changes in the glass transition temperature ($T_g$), the melting temperature ($T_m$), and mechanical behavior (storage modulus). Overall cholesterol modification resulted in no net DMA changes in the ambient to physiologic temperature range. However, as shown in FIG. 11A, appending cholesterol moieties to the urethane hard segment increased the storage modulus at lower temperatures. FIG. 3B shows unmodified Tecothane® had a $T_g$ of ~51° C. which is in accordance with previously published results[12]. In contrast, cholesterol modified polyurethane had a higher $T_g$ of –24° C. The melting temperature was approximately 112° C. for unmodified Tecothane and 73° C. for cholesterol modified Tecothane.

Figure 12A:
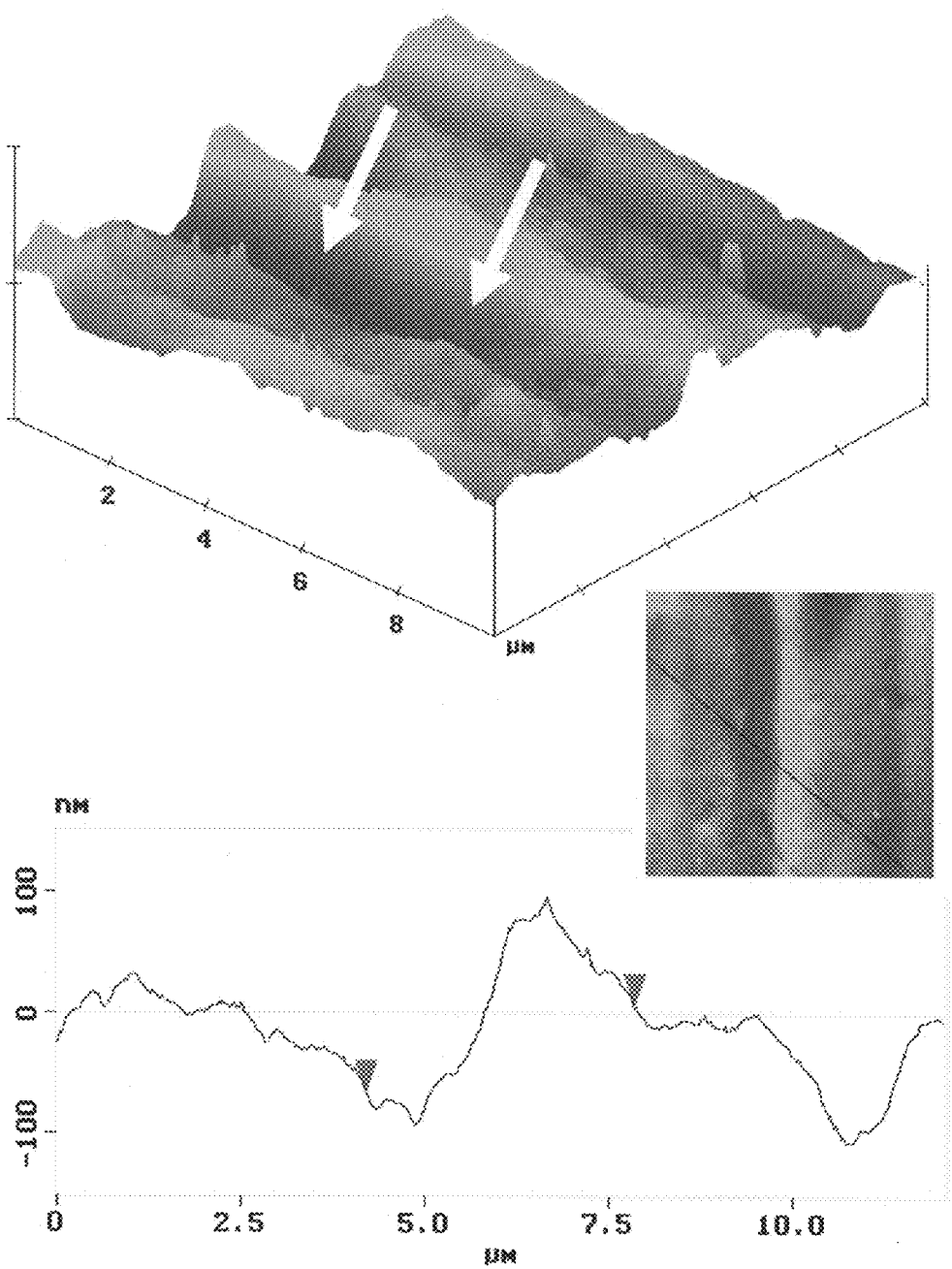
FIG. 12A and FIG. 12B are 3-dimensional and 2-dimensional (inset) atomic force microscopic images and corresponding surface measurements of unmodified polyurethane (FIG. 12A) and cholesterol modified polyurethane (FIG. 12B). Air exposed surfaces subjected to solvent evaporation are shown. The unmodified polyurethane (FIG. 12A) shows an irregular surface with grooves (indicated by arrows). In contrast the cholesterol modified polyurethane (FIG. 12A) shows a smoother surface with less pronounced irregularities.
Figure 12B:
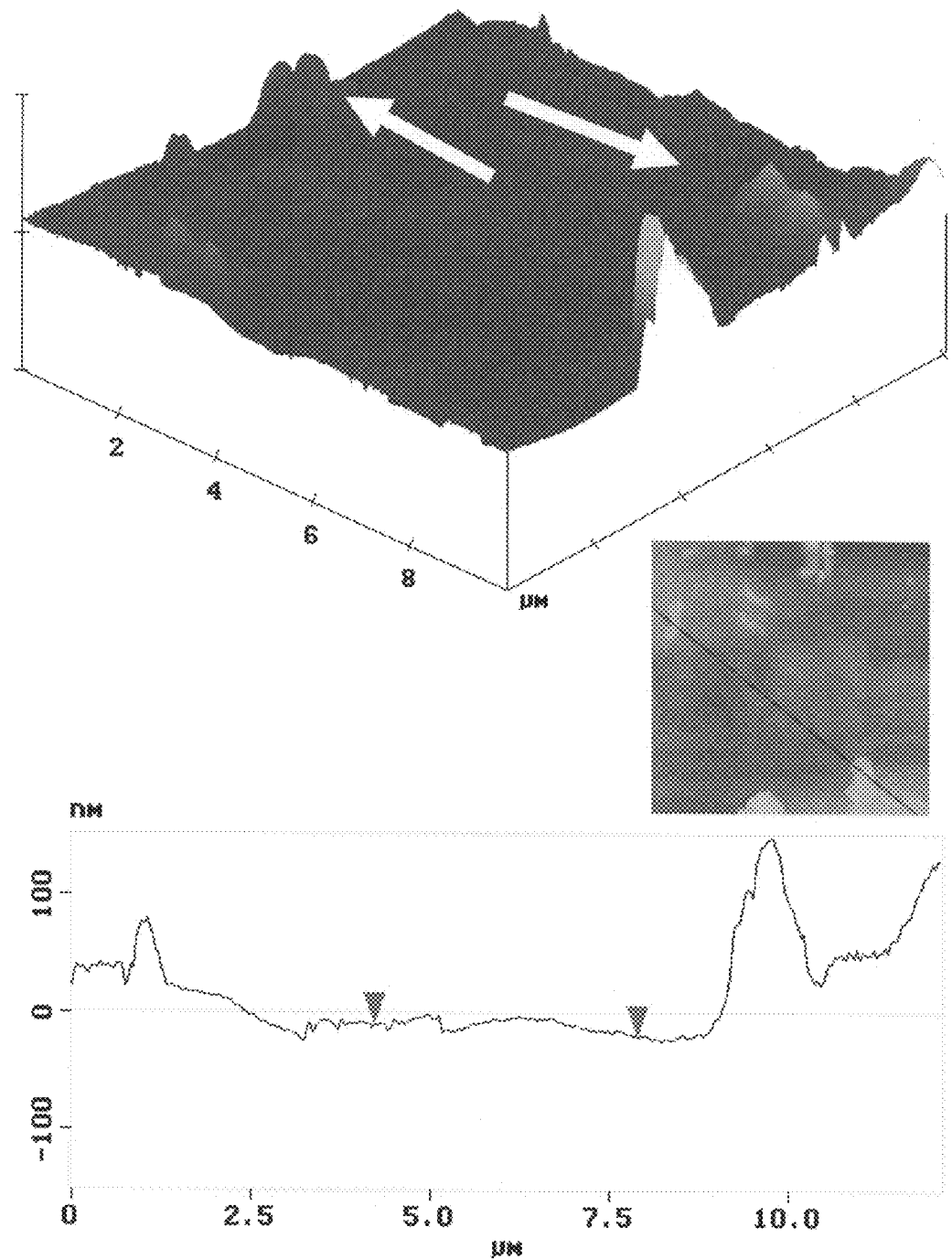

Cholesterol modified polyurethane's surface properties were compared to unmodified polyurethane in contact angle studies and AFM investigations. The contact angle of cholesterol modified polyurethane was about 30° greater than the unmodified surface. These differences are statistically significant (p=0.02) and thus demonstrate increased hydrophobicity due to covalently attached cholesterol. Atomic force microscopy studies compared the air exposed surface topography of cholesterol modified and unmodified polyurethane (FIGS. 12A and 12B). The unmodified polyurethane showed widespread ridges and valleys at the air exposed surfaces. Cholesterol modified polyurethane demonstrated qualitatively smoother surfaces with fewer surface irregularities than unmodified polyurethane. Both types of polyurethane films showed increased smoothness per AFM on the non-air exposed surfaces (data not shown).

Cell-Polyurethane Interactions

Figure 5A:
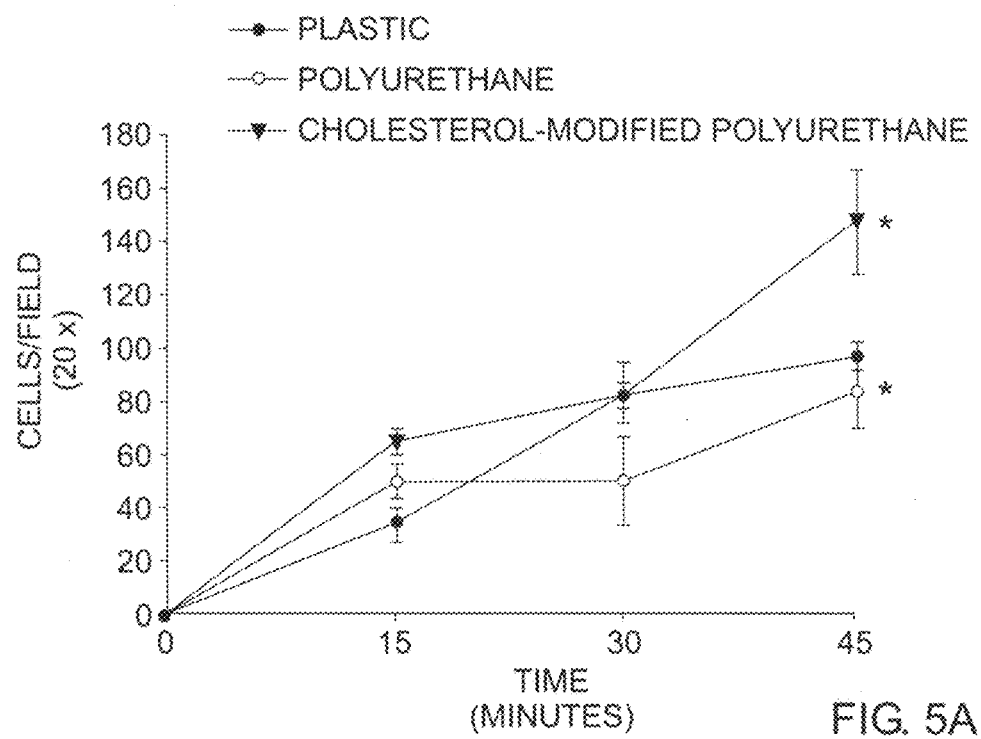
FIGS. 5A and 5B are graphical representations of the kinetics of bovine arterial endothelial cells (BAEC) attachment over a 45 minute time period to tissue culture-treated plastic (closed circles), unmodified polyurethane (open circles) and cholesterol modified polyurethane (closed triangle) in both serum free (FIG. 5A) and serum containing media (FIG. 5B). Results (mean±standard error) show significantly more endothelial cell attachment over time to the cholesterol modified polyurethane surface compared to either tissue culture treated plastic or unmodified polyurethane. Cell attachment was not dependent on serum conditions. A sign * indicates significant difference between cell attachment on cholesterol modified polyurethane and unmodified polyurethane (p=0.006) in growth media conditions. A sign ** indicates values are significantly different (p=0.0002) between cell attachment on cholesterol modified polyurethane and unmodified polyurethane in serum deficient conditions.

The kinetics of attachment of endothelial cells (BAEC's) to the cholesterol-modified polyurethane surface was compared to unmodified polyurethane and tissue culture polystyrene surfaces. BAEC's were seeded using 10% FBS supplemented medium onto the three types of surfaces and sampled every fifteen minutes quantitating attached cells. A separate study substituting serum free media for normal growth media assessed the contribution of exogenous lipids and other serum components from the supplemented media. FIG. 5A shows the average number of BAEC's per field over the 45-minute interval of the experiment. After thirty minutes, cell attachment to cholesterol modified polyurethane was not significantly different than cell attachment to either plastic or unmodified polyurethane. However, by the 45-minute cessation of the study, cell attachment on the cholesterol modified polyurethane in the presence of 10% FBS was significantly greater than observed with the unmodified polyurethane (p=0.006) (FIG. 5A). In fact more BAECs attached to the cholesterol modified polyurethane than to the tissue culture treated plastic; however, these differences were not found to be significant (p=0.070). Comparisons of cell attachment to cholesterol modified polyurethane in the presence and absence of serum (FIG. 5B) showed similar trends to the serum free studies and suggests that exogenous lipids and other serum components do not influence the initial attachment of BAEC's to cholesterol-modified polyurethane.

We compared retention of an intact endothelium, growing on either a cholesterol modified or unmodified polyurethane substrate under fluid induced mechanical forces, by quantifying the number of both BAEC's and separately BOEC's remaining on the respective substrates after a fixed time exposure to simulated arterial shear stress (25 dynes/cm$^2$). In the BAEC studies, phase microscopy (FIGS. 13 A-L) was performed to qualitatively evaluate shear stress induced changes in the endothelial cell morphology after 0.5, 1 and 2 hours. At the initiation of the study, cells growing on glass and cholesterol modified polyurethane (FIGS. 13A and 13E) showed a characteristic "cobblestone morphology". Cells growing on unmodified polyurethane (FIG. 13I) had a comparable morphology. After one hour (FIG. 13G) of exposure to fluid flow at 25 dynes/cm$^2$, cells growing on cholesterol modified polyurethane retained their morphology, and continued to do so at two hours as well (FIG. 13H). The cells cultivated on the unmodified polyurethane substrate failed to maintain intercellular organization and extensive cell loss was apparent after 1 hour (FIG. 13K). Endothelial cells continued to be shed from unmodified polyurethane up to the 2 hours conclusion of the study (FIG. 13L). Cells seeded onto NaOH treated glass slides (FIGS. 13A-D) were largely retained after 1-hour exposure to shear. However, after two hours of shear exposure, BAEC's growing on NaOH treated glass slides also demonstrated regions of detachment from the surface (FIG. 13D).

Figure 13M:
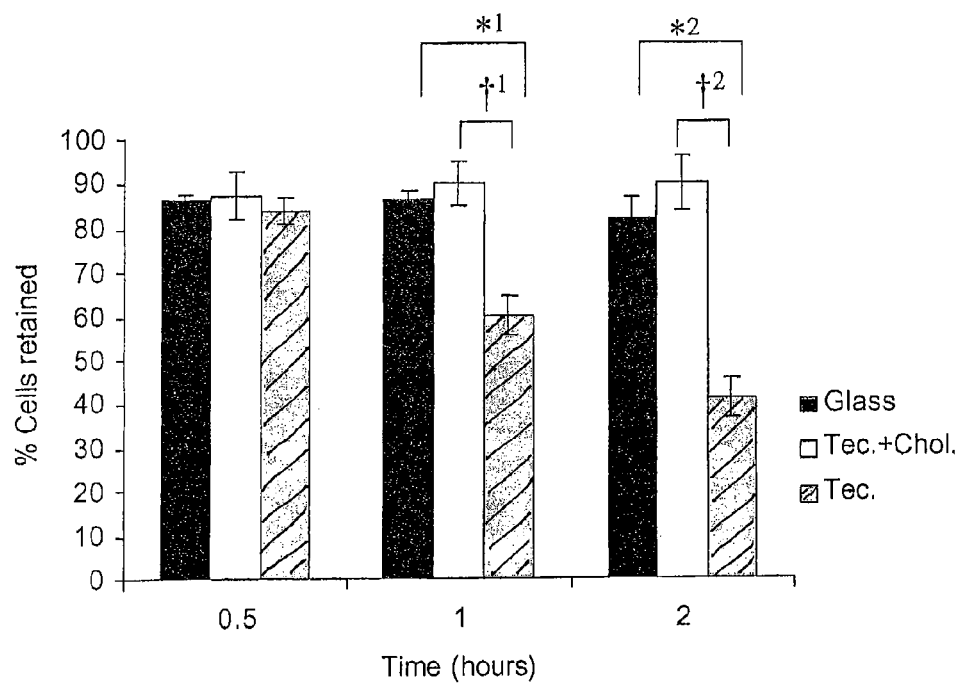
FIG. 13M is a graphical representation of BAEC retention after the indicated amount of time exposed to 25 dynes/cm$^2$. After 1 hour exposure to shear, unmodified polyurethane surfaces retained significantly fewer BAEC's than the cholesterol modified polyurethane or glass substrates. After 2 hours BAEC's cultured on glass or cholesterol modified polyurethane retain 80 and 90% of BAEC's respectively and largely retain their characteristic cobblestone appearance (Fig. D vs. Figs. H and L). In contrast almost half of BAEC's cultured on unmodified polyurethane are not retained after 2 hours. Data are mean±SEM. *$_1$p=0.0001; *$_2$p=0.002; †$_1$p=0.001; †$_2$p=0.007.

A quantitative assessment of BAEC's exposed to shear on the three test surfaces was performed. FIG. 13M shows the average percent of BAEC's retained after exposure to 25 dynes/cm$^2$ of laminar flow for 0.5, 1 and 2 hours. After 30 minutes exposure to flow, cell retention was virtually identical on the cholesterol modified polyurethane, unmodified polyurethane and the tissue culture treated glass control. However, after 60 minutes exposure to flow, there was a significantly greater (p=0.0003) endothelial cell retention on cholesterol-modified polyurethane compared to unmodified polyurethane substrates (FIG. 13M). Only 60.3%±4.5 (n=9) of the original BAEC's were retained on unmodified polyurethane when exposed to 25 dynes/cm$^2$ shear stress for only one hour. After 120 minutes exposure to 25 dynes/cm$^2$ shear flow, cell retention was two-fold higher on cholesterol modified polyurethane compared to unmodified polyurethane. These results were statistically significant (p=0.0070). In addition, cholesterol-modified polyurethane was not statistically different than NaOH treated glass in retaining endothelial cells at 2 hours.

Figure 14M:
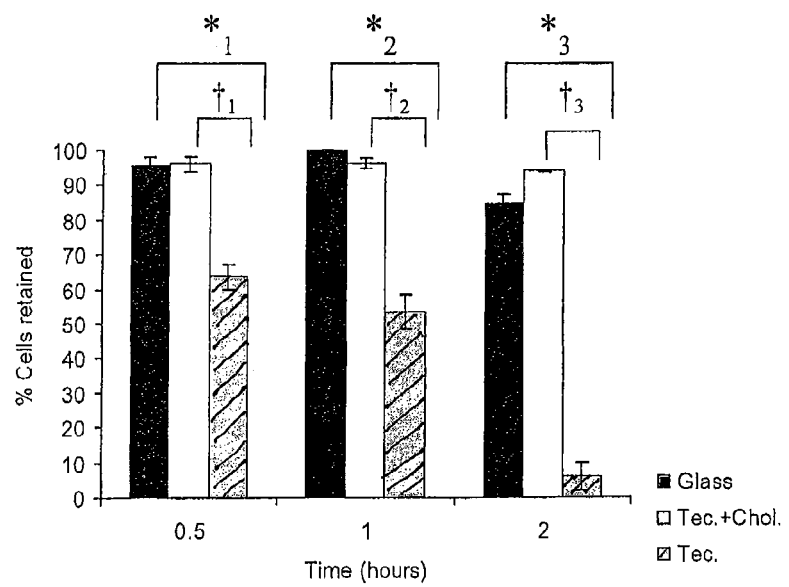
FIG. 14M is a graphical representation of BOEC retention after the indicated amount of time exposed to 25 dynes/cm$^2$. After 2 hours BOEC's cultured on glass or cholesterol modified polyurethane retained 84.2±1.1% and 90.30±3.25% of cells respectively and largely retain their characteristic cobblestone appearance (FIGS. 14D and H vs.

Blood outgrowth endothelial cells (BOEC's) are a recently characterized endothelial cell derived from a putative endothelial precursor cell in peripheral blood[7,9]. Since the use of BOEC's in vascular implant coatings is a relatively new focus, little data exists regarding the behavior of these cells under shear conditions, and no data exists on these cells seeded directly onto to polyurethane films[13]. We therefore exposed BOEC's grown to confluence on polyurethane, glass, or cholesterol modified polyurethane to 25 dynes/cm$^2$ for 0.5, 1, and 2 hours. Phase microscopy (FIG. 14 A-L) was used to evaluate changes in BOEC morphology after two hours exposure to shear at 25 dynes/cm$^2$. BOEC's seeded onto polyurethane modified cholesterol and NaOH treated glass retained their cobblestone morphology and very little cell loss was noted after two hours (FIGS. 14D and 14H). In contrast, after 0.5 or 1 hour exposure to 25 dynes/cm$^2$, significantly fewer BOEC's cultured on unmodified polyurethane (FIG. 14K) were retained compared to BOEC's cultivated on either glass or cholesterol modified polyurethane. The loss of BOEC's from the unmodified polyurethane surfaces continued throughout the experiment, and at two hours, only isolated islands of about 20 cells with evidence of cell rounding were seen throughout the film (FIG. 14L). A quantitative assessment of cell retention (FIG. 14M) showed that cholesterol modified polyurethane and tissue culture treated glass retained about 20 fold more BOEC's than the unmodified polyurethane substrate. There were no significant differences between the BOEC results (re. cell retention) on glass or cholesterol modified Tecothane (p=0.124).

This work is the first demonstration of covalent attachment of cholesterol to a polyurethane using the bromo-alkylation methodology developed by our laboratory. Mature arterial endothelial cells seeded on cholesterol modified polyurethane demonstrated significantly greater retention under simulated arterial shear stress conditions when compared to nonmodified polyurethane. These data are also the first demonstration of blood outgrowth endothelial cell adhesion directly to a modified polyurethane surface. Our BOEC data show multifold greater adhesion under arterial level shear forces on cholesterol modified polyurethane surfaces compared to unmodified polyurethane. These results imply that cholesterol modified polyurethane is hypothetically well suited for fabrication of BOEC seeded intravascular implants.

Other strategies for seeding surface-modified polyurethane with endothelial cells in order to decrease thrombogenicity have been reported. Polymerized methacrylic acid was grafted to porous polyurethane scaffolds and was shown to enhance HUVEC proliferation[14]. Zhu reported a process in which biocompatible macromolecules (collagen, chitosan, or collagen) were immobilized on an aminolyzed polyurethane surface[15]. Although both studies showed favorable proliferation results, cell retention under shear stress was not investigated.

The use of covalently attached RGD domains on polymeric biomaterials has been relatively successful in enhancing endothelial cell affinity in vascular grafts. Seifalian and colleagues characterized endothelialisation of polyurethane vascular grafts modified with a three dimensional honeycombed structure[16] as well as surface bound collagen[17] or RGD[18] or RGD/Heparin[19]. HUVEC retention with the RGD/Heparin surface under pulsatile shear flow (25 dynes/cm$^2$) was 75% when seeded upon RGD/Heparin coated polyurethane[19]. Chen and colleagues studied polyurethane crosslinked with either a commercially available epoxide or the same polyurethane coated with a cellulose binding domain RGD fusion protein contained within a gelatin matrix; human umbilical vein endothelial cells (HUVEC's) retention on these surfaces was 43% and 63% respectively, after three hour exposure to simulated arterial flow[20].

Endothelial seeded vascular grafts, composed of polytetrafluoroethylene, are currently being used in clinical trials[21, 22]. However, harvesting autologous blood vessel derived endothelial cells from patients is an important limitation. BOEC's represent an accessible endothelial cell source and both in vitro and in vivo data has demonstrated their usefulness in seeding vascular grafts[13,23-25]. Sheep studies demonstrated successful seeding of a decellularized vascular arterial heterograft using BOEC's[24]. In addition these same studies demonstrated that BOEC seeded grafts remained patent and demonstrated nitric oxide production that mediated vascular relaxation and contractile activity. Interestingly, it was noted that the seeded BOEC's had poor retention when preconditioning shear stress was raised stepwise from 1 to 25 dynes/cm$^2$ [24], when the preconditioning conditions were gradually increased very few cells were displaced[24]. Our data presented in FIG. 14M show almost complete cell retention when BOEC's were transferred from static cell culture conditions to immediate high shear stress for two hours. Thus, these prior studies clearly demonstrate the feasibility of BOEC's as a source of autologous endothelial cells for seeding vascular grafts. Similarly our data demonstrate that BOEC's can be used to directly seed our novel cholesterol modified polyurethane and remain seeded under simulated arterial shear stress conditions.

Our material characterization studies of the cholesterol modified polyurethane showed a smoothed surface topography and increased surface free energy, strongly suggesting that the modification created a lipid enriched surface. Previous work by others described the synthesis and biocompatibility of a new polyurethane formulated by combining cholesterol containing diols with disocyanates[26]. This novel polyurethane configuration had diminished platelet attachment and reduced protein absorption[26,27]. However, no studies regarding endothelial cell compatibility were reported with this cholesterol modified polyurethane.

The ideal material properties for optimal endothelial seeding have yet to be determined. Our results strongly suggest that endothelial cell attachment is at least in part a function of hydrophobic interactions between cells membrane and the surface. A similar mechanism was proposed by Sakurai and colleagues who describe cell attachment as a two step process[6]. The first step is defined as a passive attachment which involves participation of hydrophobic and van der Waals interactions[6]. The enhanced rapid affinity between BAEC's and cholesterol modified polyurethane, shown in FIG. 5, supports the view that such a passive mechanism may occur with attachment to cholesterol modified polyurethane. Their second hypothesized step[6,28] of cell attachment requires cellular interactions with the biomaterial, as reflected by the cell retention on cholesterol-modified polyurethane observed under arterial shear in the present study.

Thus, cholesterol can be covalently attached to polyurethane via bromoalkylation chemistry involving the urethane nitrogens. This modification confers profound differences in chemical, mechanical and material properties compared to unmodified polyurethane, resulting in a qualitatively smoother surface with a higher surface energy. Cholesterol modified polyurethane demonstrates significantly increased endothelial cell adhesion post-seeding under arterial shear for both mature endothelial cells and endothelial precursors.

The following examples provide further details regarding the practice of the invention. These examples are provided for illustrative purposes only, and are not intended to limit the invention in any way.

EXAMPLE I

Attachment of a Thiol Group to Cholesterol

This example describes the specific conditions employed in carrying out the reaction scheme shown in FIG. 1.

Cholesterol (5.80 g; 15 mmol; Sigma, St. Louis, Mo.) was dissolved in 76 ml dry N,N-dimethylacetamide (DMAc) under a flow of dry argon. The solution was cooled to 10° C. and 15 ml (15 mmol) of a 1.0M solution of lithium tert-butoxide in hexanes (Sigma) was added. After further cooling to 5° C., 10 ml (117 mmol) of freshly distilled epibromohydrin was added and the mixture was stirred at 3-5° C. for 2 hours. The temperature was allowed to slowly rise to 21-23° C. and the reaction was allowed to continue for another hour. The reaction mixture was then diluted with 500 ml of 0.5% aqueous KHCO$_3$ and extracted with 350 ml n-heptane and then twice more with 100 ml n-heptane. The combined organic layers were dried over Na$_2$SO$_4$. After filtration from the desiccant, the solvent was removed in vacuo. The syrupy residue (7.3 g) was purified by flash-chromatography on silica gel employing elution with hexane, hexane/toluene (1:1 mixture), and toluene. The fractions containing pure glycidyl-cholesterol (thin layer chromatography (TLC)-monitoring) were pooled and dried in vacuo until crystallization occurred. The procedure yielded 4.25 g glycidyl-cholesterol (64%). The product displayed an R$_f$ of 0.38 by TLC (silica gel, n-heptane/ethyl acetate, 85:15 by volume). The signals (only those produced by the glycidyl group not present in the starting cholesterol) obtained by $^1$H NMR analysis of the product are as follows: 2.62 and 2.87 (both m, 1H and 1H, two nonequivalent H of oxirane CH$_2$), 3.15 (m, 1H, CH), and 3.47 and 3.72 (both m, 1H and 1H, diastereotopic H of CH$_2$O).

Freshly distilled (at 115 mm Hg) thioacetic acid (4.3 ml, 60 mmol) was dissolved in DMAc (60 ml) under argon protection and cooled to −10° C. A 0.35 M freshly prepared solution of (Bu$_4$N)$_2$B$_4$O$_7$ in DMAc (42 ml, 15 mmol) was added and the temperature (which rose to −1° C.) was returned to −10° C. Glycidyl-cholesterol (4.24 g, 9.57 mmol) dissolved in DMAc (25 ml) was added and the mixture was allowed to react for 2 hours at 0° C. and then poured into ice-cold water (700 ml). The excess of thioacetic acid was distilled off in vacuo at less than 40° C. with a part of water. Approximately 100 ml of distillate was collected. The residue was extracted with 350 ml n-heptane and then 150 ml n-heptane. The organic layers were dried at 4° C. over $Na_2SO_4$, filtered and dried in vacuo. Crude 3-acetylthio-2-hydroxypropyl-cholesterol (5.9 g) was dissolved in tetrahydrofuran (THF; 30 ml) and mixed with a 2.7 M solution of $NH_2OH$ in 2-propanol (37 ml; 100 mmol) under argon. The mixture was allowed to react at room temperature for 5 hours and diluted with 1.2% aqueous $H_3PO_4$ (300 ml). Organic solvents were removed in vacuo at less than 30° C. The resultant solid precipitate was filtered off, thoroughly washed with water and dried in vacuo. Crude 3-mercapto-2-hydroxypropyl-cholesterol (4.30 g) was purified by flash-chromatography (silica gel, hexane then hexane/ethyl acetate, 10:1). The yield of pure crystalline 3-mercapto-2-hydroxypropyl-cholesterol was 3.33 g (73%). The product displayed an $R_f$ of 0.26 by TLC (silica gel, n-heptane/ethyl acetate, 85:15 by volume). The signals (only those not present in the starting cholesterol) obtained by $^1H$ NMR analysis of the product are as follows: 2.59-2.73 (m, 2H, $CH_2S$), 3.49 and 3.56 (both m, 1H and 1H, diastereotopic H of $CH_2O$), and 3.79 (m, 1H, CH).

EXAMPLE II

Preparation of Cholesterol-Modified Polyurethane

This example describes the specific conditions employed in carrying out the reaction scheme, shown in FIG. 2.

Tecothane TT-1074A (15.8 g; containing approximately 38 mmol of urethane NH groups; Thermedics Inc., Woburn, Mass.) was soaked in toluene (150 ml) for 60 hours. After removal of the excess solvent, the swollen polymer was dried in vacuo at 40° C. and dissolved in DMAc (300 ml) under a flow of dry argon. Freshly distilled (at 15 mm Hg) 1,4-dibromobutane (15 ml, 126 mmol) was added and the solution was cooled to −6° C., A 1.0 M solution of lithium tert-butoxide in hexanes (7.6 ml; 7.6 mmol; Sigma) diluted with dry DMAc (20 ml) was added over a ten minute period with vigorous stirring at −5 to −6° C. The resultant mixture was stirred at −1 to 1° C. for one hour with continued argon protection and then acidified with acetic acid (6.5 ml). The reaction mixture was poured into a large volume of cold (−55° C.) methanol (1200 ml). The resulting coagulate of polymer was separated and thoroughly washed with methanol followed by 2-propanol and subsequently dried in vacuo (0.5 mm Hg) at room temperature. The crude polymer was redissolved in dimethylformamide (DMF; 275 ml). The solution was then filtered and the polymer was precipitated with cold methanol. The precipitate was washed with large volumes of methanol and water and subsequently stirred for 16 hours with a large amount of water at 4° C. The solution was dried in vacuo (0.04 mm Hg) at room temperature to yield 15.64 g of the bromobutylated Tecothane represented in FIG. 2. $^1H$ NMR spectral analysis of bromobutylated Tecothane (see Alferiev, I. et al. 2001. J. Polym. Sci. Part A: Polym. Chem. 39:105-116) indicated that the modification of urethane sites with 4-bromobutyl groups was 20% corresponding to approximately 0.45 mmol of 4-bromobutyl groups per gram of polymer.

The bromobutylated Tecothane (1.14 g, containing approximately 0.5 mmol of 4-bromobutyl groups) described above was dissolved in DMAc (20 ml) under argon and cooled to −2° C. A solution of 3-mercapto-2-hydroxypropyl-cholesterol (0.495 g, 1.04 mmol) in DMAc (8 ml) was added and a freshly prepared 0.12 M DMAc-solution of $(Bu_4N)_2B_4O_7$ (5 ml, 6 mmol) was also added. The mixture was stirred at −1 to 1° C. for one hour and acidified with acetic acid (0.12 ml, 2 mmol). The reaction solution was then filtered and the polymer was precipitated with methanol (150 ml). The precipitate was washed with methanol alternating with 2-propanol and stirred consequently with large amounts of 2-propanol, methanol, and water and dried under 0.05 mm Hg conditions. The procedure yielded 1.31 g of cholesterol-modified Tecothane. $^1H$ NMR analysis of this polymer (DMF-$d_7$) indicated covalent attachment of cholesterol to 20% of the urethane segments via noncleavable sulfide bonds (see FIG. 2) corresponding to approximately 0.4 mmol of pendant cholesterol moieties per gram of polymer.

EXAMPLE III

Cell Adhesion to Cholesterol Modified Polyurethane

Successful cell engraftment to a biological or an artificial surface is an orchestrated, multiple step process involving cell attachment to the surface and the ability of the cells to receive appropriate physical and chemical signaling cues from the microenvironment to maintain cell viability. The cellular affinity and cell viability of cholesterol modified polyurethane was compared to unmodified polyurethane and plastic in in vitro culture environments. To determine the cellular attachment properties of the three surfaces, equal concentrations ($7.5 \times 10^4$ cells/ml) of rat cardiac smooth muscle cells (A10; American Type Culture Collection; Manassas, Va.) were dispensed into individual wells of a 24 well flat bottomed plate (BD Biosciences Falcon™; Franklin Lakes, N.J.). The well bottoms were covered with polyurethane films composed of cholesterol modified or unmodified polyurethane. Control wells had no polyurethane and presented a tissue culture treated polystyrene surface for attachment. At 15 minute intervals during the 45 minute, duration of the study, cells in all treatment groups were washed in phosphate buffered saline and fixed in paraformaldehyde. Cells were stained with a fluorescent, nuclei specific dye (4',6-diamidino-2-phenylindole; DAPI). Cell attachment was determined by counting DAPI labeled cells in 7 random fields using a Nikon (Melville, N.Y.) inverted fluorescent microscope at 20× with the appropriate fluorescent filter set.

Figure 3:
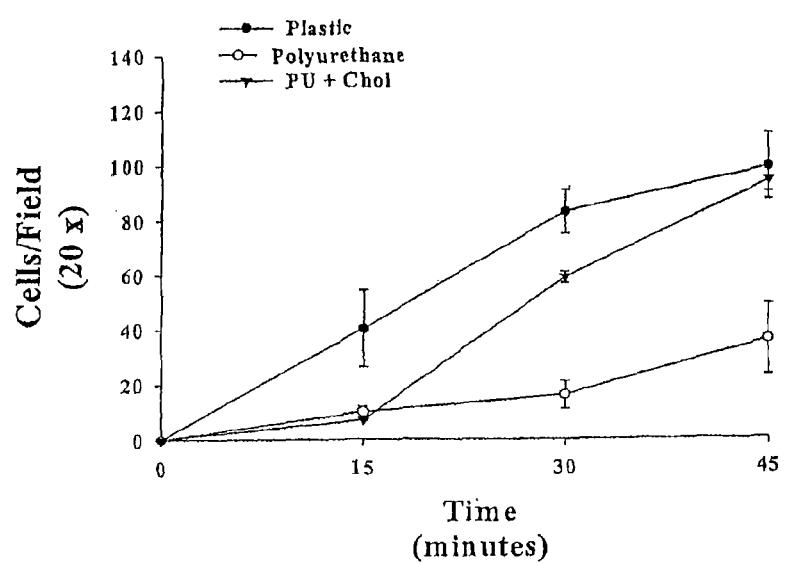
FIG. 3 is a graphic representation of the number of cells attached to tissue culture treated polystyrene, polyurethane, or cholesterol modified polyurethane (PU+Chol) per field, at 20× magnification, as a function of time.

As seen in FIG. 3, after 30 minutes the average number of cells per field attaching to the cholesterol modified polyurethane was significantly greater than cells seeding onto the unmodified polyurethane surface (p. 0.05). This trend continued for the 45 minute duration of the study. During the same time frame, cell attachment to the tissue culture treated plastic and cholesterol modified polyurethane were not significantly different and were virtually identical at the end of the 45 minute duration. These data suggest that cholesterol modified polyurethane is a suitable matrix for the attachment of cardiac myocytes.

The ability of the three matricies to sustain cell survival in culture was assessed by a commercially available LIVE/DEAD® viability/cytotoxicity kit (Molecular Probes; Eugene, Oreg.). This assay distinguishes between viable living cells, indicated by a green fluorescent label, and dead or damaged cells, indicated by a red fluorescent marker. A10 cells grown on tissue culture treated plastic, unmodified polyurethane, or cholesterol modified polyurethane were assessed for viability after seven days in culture. Representative photomicrographs assessing cell viability in A10 cells grown on the indicated substrates for seven days. Cells grown on plastic were about 80% confluent and have an elongated bipolar morphology typical of a smooth muscle cell. There appears to be little or no cell distress as indicated by minimal fluorescent red labeling. In contrast, A10 cells grown for seven days on unmodified polyurethane had a markedly different morphology appearing more rounded than A10 cells grown on plastic. The extensive red fluorescent labeling and reduced cell number compared to those cells grown on plastic indicate that this cell, culture is clearly distressed and not viable. Appending cholesterol to the polyurethane maintains the overall morphology of the A10 cells. Analysis of the viability of these cultures show that the culture is rather healthy as indicated by the widespread green fluorescent labeling and confluence approaching that of cells grown on a plastic surface. These data show that cholesterol modified polyurethane is superior to unmodified polyurethane and is equivalent to tissue culture treated plastic in maintaining cell viability.

Endothelial cells serve a vital role in promoting thromboresistance in the microvasculature. A biocompatible material that is amenable to endothelial cell seeding could be useful in maintaining a clot free vascular implant. An attachment assay, as detailed above, examined the affinity of bovine arterial endothelial cells to the cholesterol modified polyurethane. In addition, substituting serum free media for normal growth media assessed the contribution of exogenous lipids from supplemented serum in the media. The average number of bovine arterial endothelial cells per field over the 45-minute duration of the experiment is shown in FIG. 5A. After 30 minutes, cell attachment to cholesterol modified polyurethane film was identical to cell attachment to tissue culture treated plastic. However at the 45-minute timepoint of the study, cell attachment to modified polyurethane was significantly greater (p. 0.05) than to plastic. A comparison of cholesterol modified polyurethane to the unmodified control polyurethane shows that cell attachment to the cholesterol modified polyurethane was more than twice that to the unmodified polyurethane.

Figure 5B:
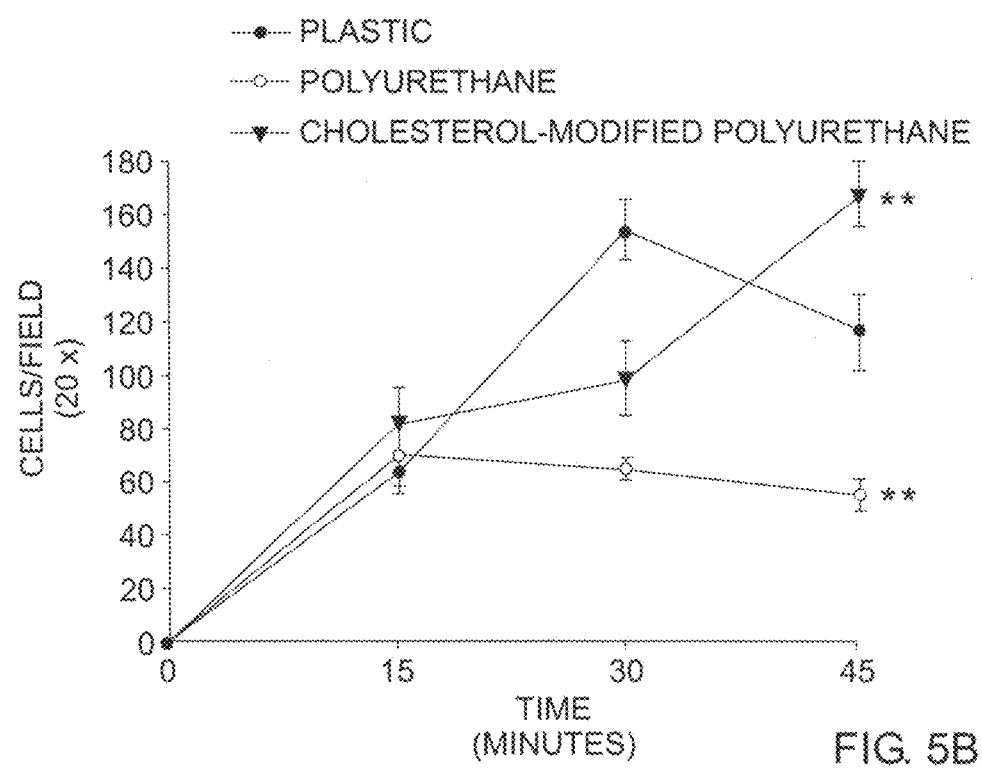

Similar trends were noted in attachment assays performed in serum free media (FIG. 5B). After 30 minutes cell attachment to cholesterol modified polyurethane film was greater than to tissue culture treated plastic with significant (p. 0.05) differences occurring at the 45 minute timepoint of the study. About three times as many cells were attached to the modified polyurethane than to the unmodified polyurethane after 45 minutes. Comparing cell attachment to cholesterol modified polyurethane in the presence and absence of serum showed no differences in values over time strongly suggesting that exogenous lipids in the serum do not influence the attachment of cells to the cholesterol. In addition, these data show that endothelial cells have a higher affinity to cholesterol modified polyurethane than to tissue culture treated plastic or unmodified polyurethane.

EXAMPLE IV

Cell Adhesion Under Laminar Flow Conditions

Figure 6:
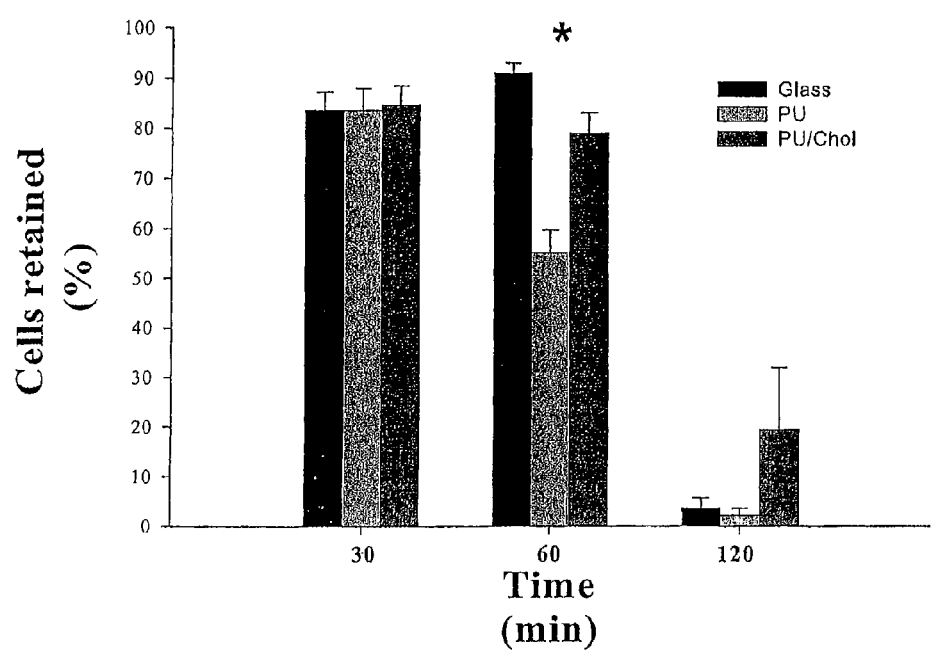
FIG. 6 is a graphical representation of the degree of bovine arterial endothelial cell attachment to several different matrices (glass=tissue culture treated glass; PU=polyurethane coated glass; PU/Chol=cholesterol modified polyurethane coated glass) at various time points in the presence of a laminar flow of media at 25 dynes/cm$^2$.

The cell attachment properties of polyurethane and cholesterol modified polyurethane using bovine aortic endothelial cells (BAEC's) under physiological relevant laminar flow conditions were analyzed. Briefly, BAEC's were grown until confluence on tissue culture treated glass microscope slides or slides coated with Tecothane±appended cholesterol, which was generated as described hereinabove. The slides were subsequently attached to a parallel plate laminar flow chamber and media was passed over the cells at 25 dynes/cm$^2$ for variable lengths of time. After the indicated times, attached cells were counted using the nuclei specific stain 4',6-diamidino-2-phenylindole, dihydrochloride (DAPI). Cell retention was calculated as a percentage of cells not exposed to shear flow. As seen in FIG. 6, tissue culture treated glass and cholesterol modified polyurethane retained 86.76±7.7 and 89.3±13.8 of the original cells after 30 minutes of flow, respectively. After one hour, however, unmodified polyurethane retained only 51.37±11.8% of the original BAEC population while tissue culture treated glass and cholesterol modified polyurethane retained a similar number of cells as after 30 minutes of laminar flow. After 2 hours of laminar flow, cholesterol modified polyurethane was able to retain significantly more endothelial cells than either polyurethane or tissue culture treated glass (FIG. 6). These data show that appending lipids to polyurethane vastly improves the ability of the matrix to retain cells exposed to shear flow.

The foregoing examples demonstrate the lipid derivatized polyurethanes of the instant invention do not induce apoptosis or calcification of cells grown on the matrix. Indeed, cells seeded on lipid derivatized polyurethane attached to the matrix strongly (see Example IV) and thrived as compared to cells grown on other matrices (see, e.g., FIGS. 5A and B).

A number of literature and patent references are cited in the foregoing application in order to more fully describe the state of the art to which this invention pertains. The disclosure of each of these citations is incorporated by reference herein.

Further provided is a method of treating or preventing a condition in a patient, said method comprising implanting in the patient an implant coated with cells, such that the cells are administered to the patient to treat or prevent the condition, wherein the cells are releasably attached to the implant by a lipid substituent pendant from at least one urethane nitrogen and/or at least one carbon atom of a polyurethane component of the implant. Non-limiting examples of condition are thrombosis and inflammatory cell interactions.

The invention will be illustrated in more detail with reference to the following Examples, but it should be understood that the present invention is not deemed to be limited thereto.

EXAMPLE V

Figure 17A:
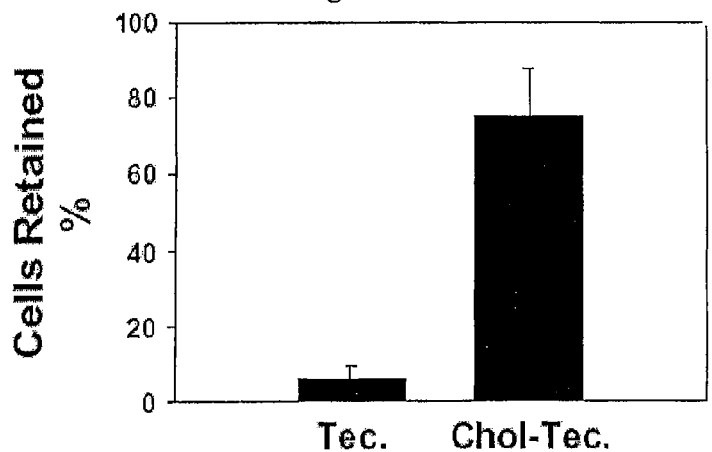
Figure 17B:
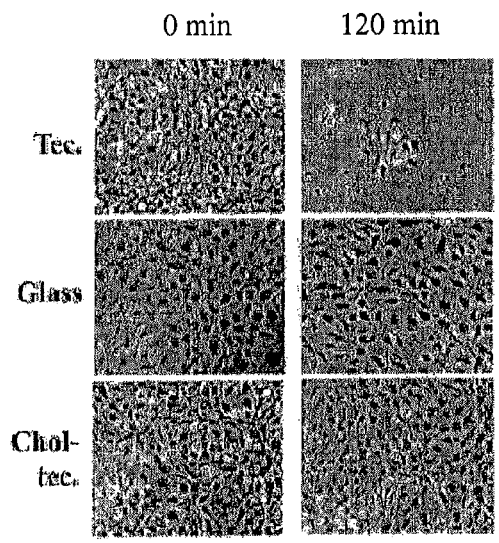

FIGS. 17A and B demonstrate high shear (2 hour at 25 dyne/cm$^2$) adhesion on cholesterol modified but not on unmodified with endothelial precursor cells. In FIGS. 18 A and B, a higher shear used, 75 dynes/cm2 for 2 hours is significant since it is typical heart valve level shear force. Also shown are the first results we have demonstrating retention of seeded endothelial cells on cholesterol modified polyurethane in blood stream implants.

EXAMPLE VI

Figure 4A:
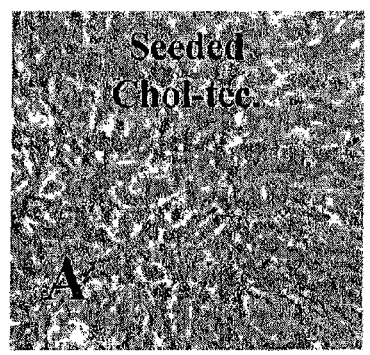
FIG. 4A and FIG. 4B are photomicrographs of cholesterol modified polyurethane heart valve leaflets seeded with endothelial precursor cells before implantation and after 30 days after implantation.
Figure 4B:
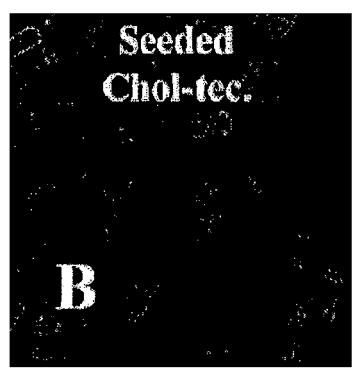
Figure 4C:
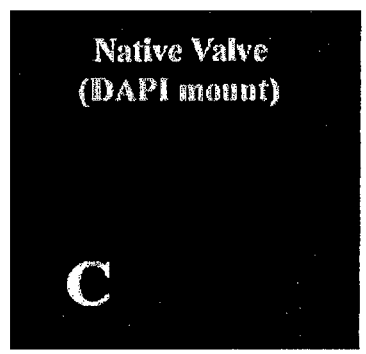
FIG. 4C is a photomicrographs of a native heart valve before implantation, which was used for comparison.
Figure 4D:
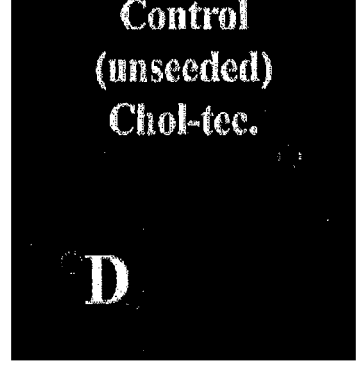
FIG. 4D is a photomicrograph of unseeded cholesterol modified polyurethane heart valve leaflet (control) after 30 days.

Cholesterol modified polyurethane heart valve leaflets were prepared and were seeded with endothelial precursor cells. Photomicrographs (see FIGS. 4A-4D) show results before and after 30 day pulmonary valve implantation in sheep demonstrating pre-implant confluence (FIG. 4A), and an endothelial monolayer (FIG. 4B), with no endothelium developing in unseeded leaflet implants (FIG. 4D); a native heart valve was used for comparison (FIG. 4C).

EXAMPLE VII

TABLE I

Dynamic Mechanical Analyses Results, Cholesterol Modified Tecothane versus Unmodified Techothane with and without Peroxide-Co Oxidative Exposure

| Configuration | $H_2O$ | $H_2O_2$ |
|---|---|---|
| Tecothane | −40° C. | −29.78° C. |
| Tecothane-Cholesterol | −6° C. | −8° C. |

Glass transition temperature (Tg) of tecothane configurations exposed to water or oxidative degradation ($H_2O_2$ and $CoCl_2$) for 14 days at room temperature.

TABLE II

Contact Angle Results, Cholesterol Modified Tecothane versus Unmodified Techothane with and without Peroxide-Co Oxidative Exposure

| Configuration | $H_2O$ | $H_2O_2$ |
|---|---|---|
| Tecothane | 80.61 ± 3.5 | 68.7 ± 0.03 |
| Tecothane-Cholesterol | 98.47 ± 2.37 | 72.97 ± 6.65 |

Figure 15:
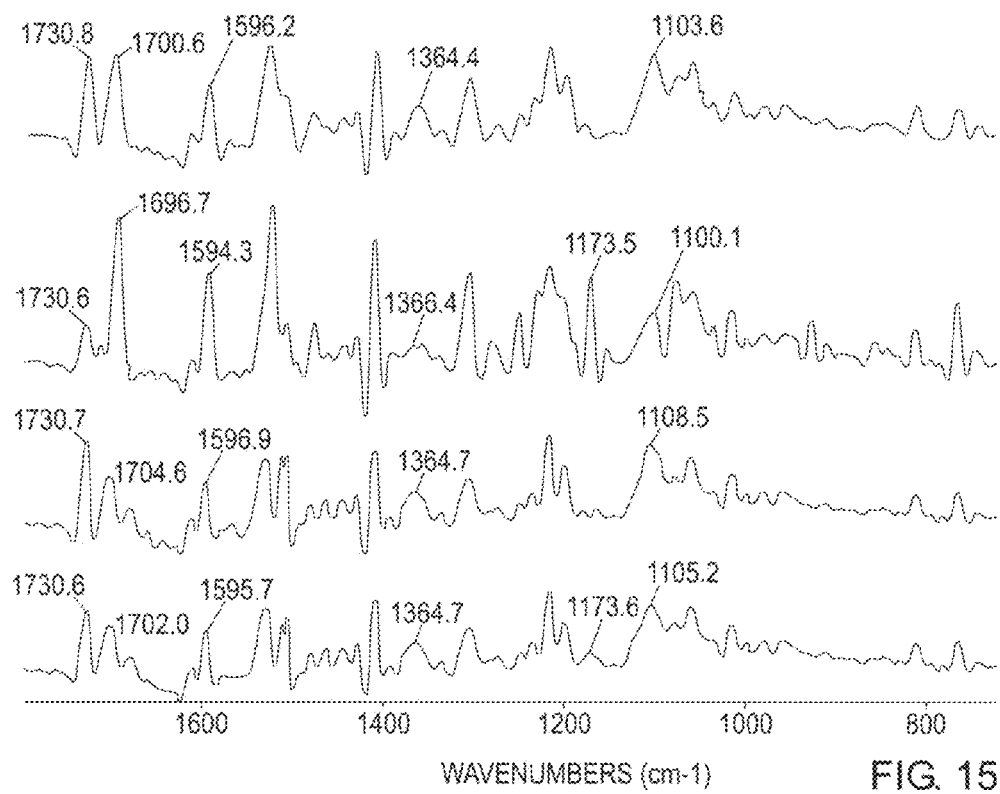
FIG. 15 is FTIP spectra demonstrating examples of the 1173 peak change that occurs during oxidation and is reduced by cholesterol modification of polyurethane.

The FTIR curves shown in FIG. 15 demonstrate examples of the 1173 peak change that occurs during oxidation and is reduced by cholesterol.

Figure 16:
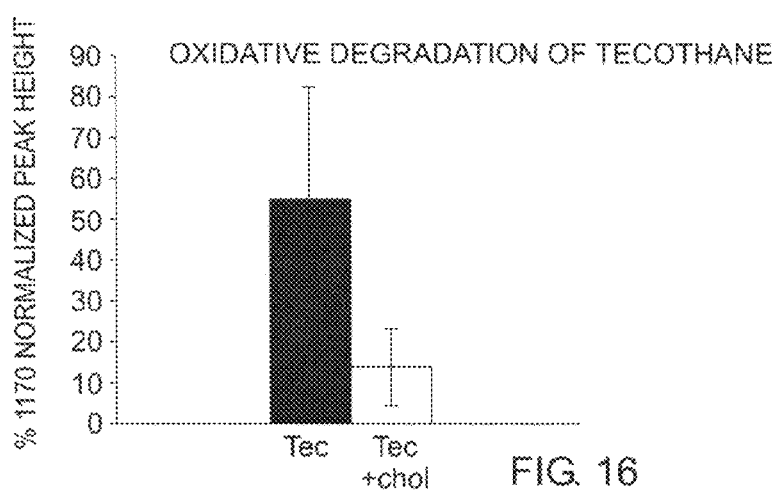
FIG. 16 is a block diagram showing oxidative degradation of unmodified polyurethane (a black block) and cholesterol-modified polyurethane (a white block).

The FTIR data from a peroxide-cobalt oxidation study are further summarized as shown in FIG. 16.

While the invention has been described in detail and with reference to specific examples thereof, it will be apparent to one skilled in the art that various changes and modifications can be made therein without departing from the spirit and scope thereof.

REFERENCES

1. Alferiev I, Vyavahare N, Song C, Levy R J. Elastomeric polyurethanes modified with geminal bisphosphonate groups. J Polym Sci 2001; 39:105-116.
2. Wisman C B, Pierce W S, Donachy J H, Pae W E, Myers J L, Prophet G A. A polyurethane trileaflet cardiac valve prosthesis: in vitro and in vivo studies. ASAIO Transactions. 1982; 28:164-8.
3. Alferiev I, Fishbein I. Activated polyurethane modified with latent thiol groups. Biomaterials 2002; 23:4753-4758.
4. Alferiev I, Stachelek S J, Lu Z, Fu A L, Sellaro T L, Connolly J M, Bianco R W, Sacks M S, Levy R J. Prevention of polyurethane valve cusp calcification with covalently attached bisphosphonate diethylamino moieties. J Biomed Mater Res 2003; 66A:385-95.
5. Stachelek S J, Song C, Alferiev I, Defelice S, Cui X, Connolly J M, Bianco R W, Levy R J. Localized gene delivery using antibody tethered adenovirus from polyurethane heart valve cusps and intra-aortic implants. Gene Ther 2004; 11:15-24.
6. Okano T, Yamada N, Okuhara M, Sakai H, Sakurai Y. Mechanism of cell detachment from temperature-modulated, hydrophilic-hydrophobic polymer surfaces. Biomaterials 1995; 16:297-303.
7. Lin Y, Weisdorf D J, Solovey A, Hebbel R P. Origins of circulating endothelial cells and endothelial outgrowth from blood. J. Clin Invest 2000; 105:71-7.
8. Lin Y, Chang L, Solovey A, Healey J F, Lollar P, Hebbel R P. Use of blood outgrowth endothelial cells for gene therapy for hemophilia A. Blood. 2002; 99:457-62.
9. Solovey A, Lin Y, Browne P, Choong S, Wayner E, Hebbel R P. Circulating activated endothelial cells in sickle cell anemia. New Eng J of Med 1997; 337:1584-90.
10. Tamada A, Ikada Y. Fibroblast growth on polymer surfaces and biosynthesis of collagen. J Biomed Mater Res 1994; 25:783-9.
11. Frangos J. Shear stress induced stimulation of mammalian cell metabolism. Biotech and Bioeng 1988; 32:1053-1060.
12. Yang M, Zhang Z, Hahn C, Laroche G, King M W, Guidon R. Totally Implantable Artificial Hearts and Left Ventricular Assist Devices: Selecting Impermeable Polycarbonate Urethane to Manufacture Ventricles. J Biomed Mat Res 1999; 48:13-23.
13. He H, Shirota T, Yasui H, Matsuda T. Canine endothelial progenitor cell-lined hybrid vascular graft with nonthrombogenic potential. J Thorac Cardiovasc Surg 2003; 126: 455-64,
14. Zhu Y, Gao C, Guan J, Shen J. Engineering porous polyurethane scaffolds by photografting polymerization of methacrylic acid for improved endothelial cell compatibility. J Biomed Mater Res 2003; 67A:1367-1373.
15. Zhu Y, Gao C, He T, Shen J. Endothelium regeneration on luminal surface of polyurethane vascular scaffold modified with diamine and covalently grafted with gelatin. Biomaterials 2004; 25:423-430.
16, Salacinski H J, Tai N R, Punshon G, Giudiceandrea A, Hamilton G, Seifalian A M. Optimal endothelialisation of a new compliant poly(carbonate-urea)urethane vascular graft with effect of physiological shear stress. Eur J Vasc Endovasc Surg 2000; 20:342-52.
17. Salacinski H J, Punshon G, Krijgsman B, Hamilton G, Seifalian A M. A hybrid compliant vascular graft seeded with microvascular endothelial cells extracted from human omentum. Art Org 2001; 25:974-82.
18. Krijgsman B, Seifalian A M, Salacinski H J, Tai N R, Punshon G, Fuller B J, Hamilton G. An assessment of covalent grafting of RGD peptides to the surface of a compliant poly(carbonate-urea)urethane vascular conduit versus conventional biological coatings: its role in enhancing cellular retention. Tis Eng 2002; 8:673-80.
19. Tiwari A, Salacinski H J, Punshon G, Hamilton G, Seifalian A M. Development of a hybrid cardiovascular graft using a tissue engineering approach. FASEB Journal 2002; 16:791-6.
20. Hsu S-h, Sun S-h, Chen D. Improved Retention of Endothelial Cells Seeded on Polyurethane Small-diameter Vascular Grafts Modified by a Recombinant RGD-containing Protein. Art Org 2003; 27:1068-1078.
21. Deutsch M, Meinhart J, Fischlein T, Preiss P, Zilla P. Clinical autologous in vitro endothelialization of infrainguinal ePTFE grafts in 100 patients: a 9-year experience. Surg 1999; 126:847-55.
22. Laube H R, Duwe J, Rutsch W, Konertz W. Clinical Experience With Autologous Endothelial Cell-Seeded Polytetrafluoroethylene Coronary Artery Bypass Grafts. J Thorac Cardiovasc Surg 2000; 120:134-41.
23. Shirota T, He H, Yasui H, Matsuda T. Human endothelial progenitor cell-seeded hybrid graft: proliferative and antithrombogenic potentials in vitro and fabrication processing. Tis Eng 2003; 9:127-36.
24. Kaushal S, Amiel G E, Guleserian K J, Shapira O M, Perry T, Sutherland F W, Rabkin E, Moran A M, Schoen F J, Atala A and others. Functional small-diameter neovessels created using endothelial progenitor cells expanded ex vivo. [see comment]. Nat Med 2001; 7:1035-40.

25. Dvorin E L, Wylie-Sears J, Kaushal S, Martin D P, Bischoff J. Quantitative evaluation of endothelial progenitors and cardiac valve endothelial cells: proliferation and differentiation on poly-glycolic acid/poly-4-hydroxybutyrate scaffold in response to vascular endothelial growth factor and transforming growth factor beta1. Tis Eng 2003; 9:487-93.

26. Li Y J, Shibata Y, Nakaya T. Synthesis and characterization of polyurethanes containing cholesterol and phosphatidylcholine analagous moieties. Macromol Rap Comm 1995; 16:253.

27. Li Y J, Yokawa T, Matthews K H, Chen T M, Wang Y F, Kodama M, Nakaya T. Synthesis and blood compatibility evaluation of segmented polyurethanes based on cholesterol and phosphatidylcholine analogous moieties. Biomaterials 1996; 17:2179-89.

28. Kim J H, Kim S H, Kim H K, Akaike T, Kim S C. Adhesion and growth of endothelial cell on amphiphilic PU/PS IPN surface: effect of amphiphilic balance and immobilized collagen. J Biomed Mater Res 2002; 62:613-621.

What is claimed is:

1. An implant produced by a process comprising the steps of:

providing a modified polyurethane comprising a lipid substituent pendant from at least one urethane nitrogen and/or at least one carbon atom of the modified polyurethane, wherein the lipid substituent is a thiol-modified cholesterol substituent or an amino-modified cholesterol substituent forming an article from the modified polyurethane; and contacting the article with cells to attach the cells to the lipid substituent and thereby attach the cells to the article to form the implant, provided that a portion of the cells remains attached to the implant when exposed to a fluid-induced shear stress.

2. The implant of claim 1, wherein the implant is a member selected from the group consisting of an artificial heart; cardiac pacer leads; automatic implantable cardiodefibrillator leads; a prosthetic heart valve; a cardiopulmonary bypass membrane; a ventricular assist device; an annuloplasty ring; a dermal graft; a vascular graft; a vascular stent; cardiovascular stent; a structural stent; a catheter; a guide wire; a vascular shunt; a cardiovascular shunt; a dura mater graft; a cartilage graft; a cartilage implant; a pericardium graft; a ligament prosthesis; a tendon prosthesis; a urinary bladder prosthesis; a pledget; a suture; a permanently in-dwelling percutaneous device; an artificial joint; an artificial limb; a bionic construct; and a surgical patch.

3. The implant of claim 1, wherein the cells are blood outgrowth endothelial cells.

4. A method of treating a patient comprising providing the implant of claim 1, wherein the implant is seeded with blood outgrowth endothelial cells.

* * * * *

UNITED STATES PATENT AND TRADEMARK OFFICE
CERTIFICATE OF CORRECTION

| | | |
|---|---|---|
| PATENT NO. | : 8,465,542 B2 | Page 1 of 1 |
| APPLICATION NO. | : 13/487984 | |
| DATED | : June 18, 2013 | |
| INVENTOR(S) | : Robert J. Levy, Ivan Alferiev and Stanley J. Stachelek | |

It is certified that error appears in the above-identified patent and that said Letters Patent is hereby corrected as shown below:

In the Claims

At Column 30, line 3, Claim 1, after the hyphenated word "substituent" please insert a -- ; --.

Signed and Sealed this
First Day of April, 2014

Michelle K. Lee
*Deputy Director of the United States Patent and Trademark Office*